US010948394B2

United States Patent
Lee et al.

(10) Patent No.: US 10,948,394 B2
(45) Date of Patent: Mar. 16, 2021

(54) ULTRASOUND IMAGE-BASED CONCENTRATION MEASUREMENT

(71) Applicant: Massachusetts Institute of Technology, Cambridge, MA (US)

(72) Inventors: John Haeseon Lee, Cambridge, MA (US); Brian W. Anthony, Cambridge, MA (US); Duane S. Boning, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 613 days.

(21) Appl. No.: 15/738,544

(22) PCT Filed: Jun. 24, 2016

(86) PCT No.: PCT/US2016/039210
§ 371 (c)(1),
(2) Date: Dec. 20, 2017

(87) PCT Pub. No.: WO2016/210246
PCT Pub. Date: Dec. 29, 2016

(65) Prior Publication Data
US 2020/0041400 A1 Feb. 6, 2020

Related U.S. Application Data

(60) Provisional application No. 62/184,093, filed on Jun. 24, 2015.

(51) Int. Cl.
*G01N 15/06* (2006.01)
*G01N 29/46* (2006.01)
(Continued)

(52) U.S. Cl.
CPC ......... *G01N 15/06* (2013.01); *A61B 8/4488* (2013.01); *A61B 8/5207* (2013.01);
(Continued)

(58) Field of Classification Search
None
See application file for complete search history.

(56) References Cited

U.S. PATENT DOCUMENTS 6,481,268 B1 * 11/2002 Povey .................... G01N 15/02
73/61.75
6,585,647 B1    7/2003 Winder
(Continued)

OTHER PUBLICATIONS

Mercado, Karla P. et al., "Estimating Cell Concentration in Three-Dimensional Engineered Tissues Using High Frequency Quantitative Ultrasound", Annuals of Biomedical Engineering, vol. 42, No. 6, Jun. 2014, pp. 1292-1304.
(Continued)

*Primary Examiner* — Daniel S Larkin
(74) *Attorney, Agent, or Firm* — Strategic Patents, P.C.

(57) ABSTRACT

The systems and methods of the present disclosure are directed to ultrasound-based concentration measurement techniques in which both scatterer count and image volume are measured concurrently to provide absolute concentration measurements. In particular, through the techniques of the present disclosure, the effective thickness of an ultrasound beam can be determined based on the spreading of individual scatterers within ultrasound images. Based on the effective thickness of the ultrasound beam, the volume of the image and, thus, the concentration of particles in the image can be determined directly, without the need for estimation, approximation, or use of a reference sample.

20 Claims, 26 Drawing Sheets

(51) Int. Cl.
    *G01N 29/032* (2006.01)
    *G01N 15/10* (2006.01)
    *A61B 8/00* (2006.01)
    *A61B 8/08* (2006.01)
    *G01N 29/24* (2006.01)

(52) U.S. Cl.
    CPC .............. *A61B 8/5223* (2013.01); *A61B 8/54* (2013.01); *A61B 8/58* (2013.01); *G01N 15/10* (2013.01); *G01N 29/032* (2013.01); *G01N 29/46* (2013.01); *G01N 29/24* (2013.01); *G01N 2015/1062* (2013.01); *G01N 2291/02809* (2013.01); *G01N 2291/044* (2013.01); *G01N 2291/106* (2013.01)

(56) References Cited

U.S. PATENT DOCUMENTS

| | | | |
|---|---|---|---|
| 7,914,451 | B2 | 3/2011 | Davies |
| 8,915,852 | B2 | 12/2014 | Franceschini et al. |
| 2005/0150275 | A1 | 7/2005 | Panetta et al. |
| 2012/0227473 | A1 | 9/2012 | Sinha |
| 2014/0088429 | A1 | 3/2014 | Lomes et al. |
| 2014/0147013 | A1* | 5/2014 | Shandas ............... A61B 8/5246 382/107 |

OTHER PUBLICATIONS

Mercado, Karla P. et al., "Estimating Cell Concentration in Three-Dimensional Engineered Tissues Using High Frequency Quantitative Ultrasound", Annals of Biomedical Engineering DOI: 10.1007/s10439-014-0994-8, Feb. 28, 2014, 13 Pages.

Hughes, S.W. et al., "Volume Estimation From Multiplanar 2D Ultrasound Images Using a Remote Electromagnetic Position and Orientation Sensor", Ultrasound in Med. & Biol., vol. 22, No. 5, 1996 Nov. 21, 1995 , pp. 561-572.

Hruska, David P. et al., "Improved Parameter Estimates Based on the Homodyned K Distribution", IEEE Transaction on Ultrasonics, Ferroelectrics, and Frequency Control, vol. 56, No. 11, Nov. 2009, pp. 2471-2481.

ISA, "PCT Application No. PCT/US16/39210 International Search Report and Written Opinion dated Feb. 7, 2017", 19 pages.

EPO, "PCT Application No. PCT/US16/39210 Partial Search Report dated Dec. 12, 2016", 8 pages.

Lee, John H. et al., "Ultrasound Image-based Absolute Concentration Measurement Technique for Material with Low Scatterer Concentration", 2015 IEEE International Ultrasonics Symposium Proceedings, pp. 1-4.

WIPO, "PCT Application No. PCT/US16/39210 International Preliminary Report on Patentability dated Jan. 4, 2018", 13 pages.

\* cited by examiner

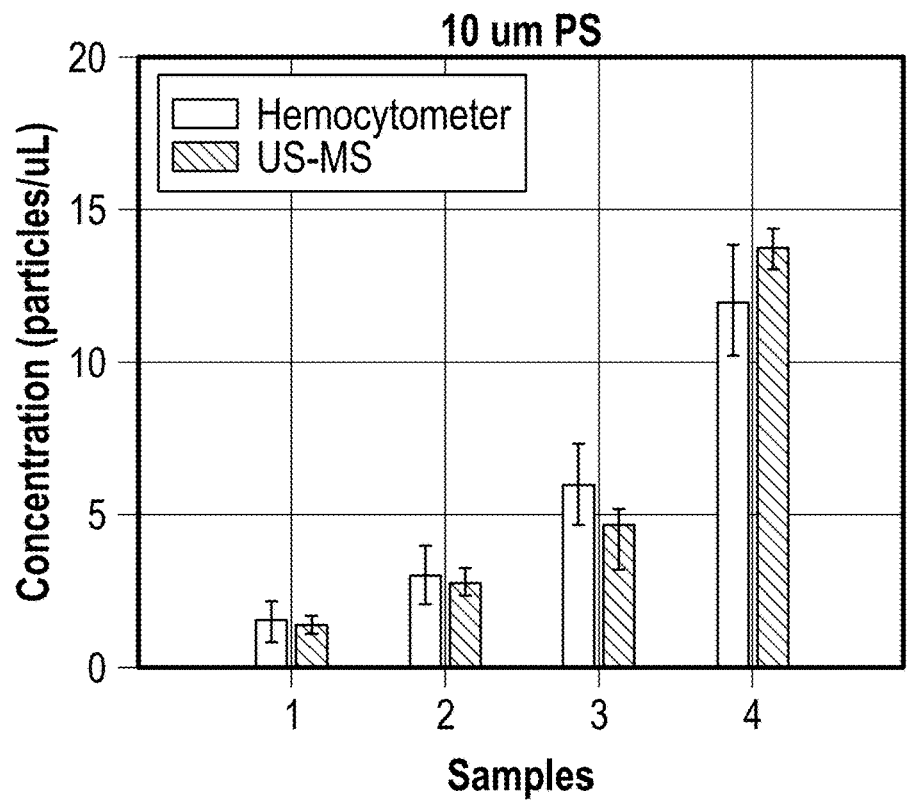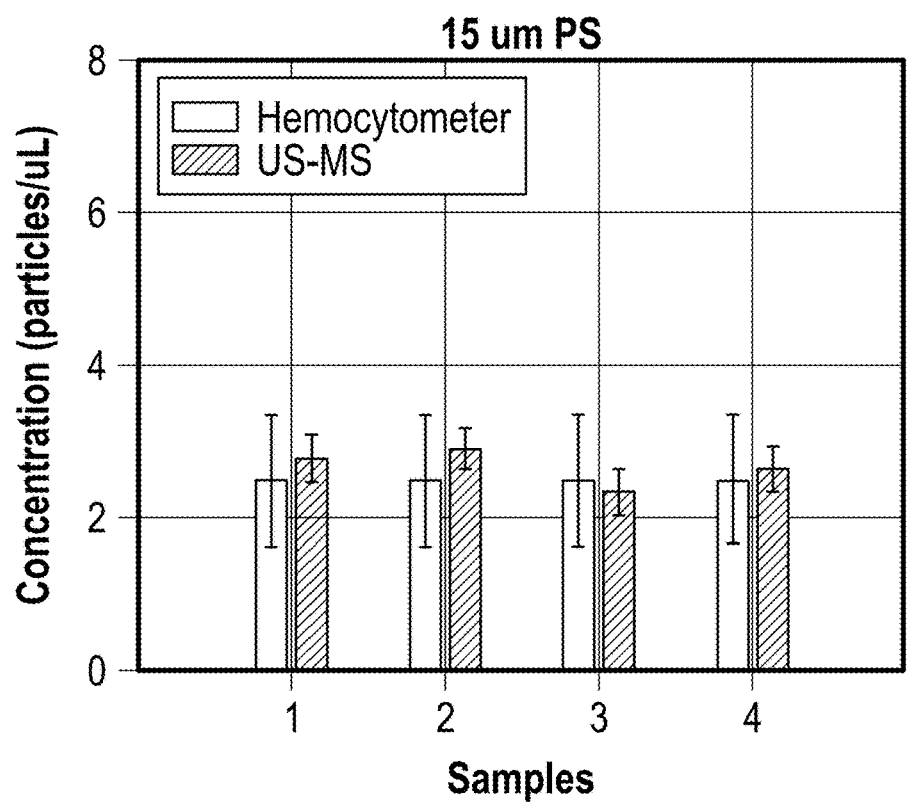
FIG. 17

ULTRASOUND IMAGE-BASED CONCENTRATION MEASUREMENT

CROSS-REFERENCE TO RELATED APPLICATIONS

This application is a national stage entry application of International Patent Application No. PCT/US16/39210 filed on Jun. 24, 2016, which claims priority to U.S. Provisional Patent Application No. 62/184,093 filed Jun. 24, 2015, where the entire contents of each of the foregoing are incorporated herein by reference.

BACKGROUND

Concentration measurement of particles in suspension is an important procedure performed in various industries including basic biology, pharmaceutics, and clinical medicine. In biological and biotechnological laboratories, cell concentration is routinely measured to monitor cell growth and the progression of experiments. In clinical laboratories, white blood cell (WBC) and red blood cell (RBC) concentrations are key parameters measured for blood and cerebrospinal fluid (CSF) samples.

Commonly used methods of measuring the concentration of particles in suspension include using a hemocytometer, using a Coulter counter, and flow cytometry-based concentration measurements. A common weakness among these methods is that they are typically destructive in the sense that the sample is discarded after analysis. This can be disadvantageous when the sample volume is small and/or difficult to acquire, thus limiting the amount of sample that can be used for analysis, and lowering the accuracy, especially when concentration is low. Further, each of these methods requires extraction of the sample from the body through an invasive procedure, such as a venipuncture or lumbar puncture, which in itself creates risk of infection and/or complication. Further, with each of these methods, the sample is removed from its innate environment and placed at risk of contamination and degradation.

Ultrasound has been used to estimate concentration of scatterers when a material is dilute and a scatterer size is similar to the wavelength produced by ultrasound, so that individual scatterers can be distinguished in an ultrasound image. The actual shape of an ultrasound beam, however, may vary significantly based on the medium being imaged, the interface between an ultrasound transducer and the scanned object, and a variety of other factors. Because of these variations in the beam shape, the image volume is not known. Thus, while the number of individual scatterers can be counted in an ultrasound image, concentration determinations are limited by imprecise knowledge of the actual shape of the ultrasound beam and, thus, of the image volume. To address this limitation, a variety of techniques have been developed for estimating concentration based on overall backscatter energy and assumptions about the geometry of an ultrasound scan. These estimation techniques, however, are based on generalized assumptions about the shape of the ultrasound beam and the scan geometry, and/or require a priori calibration of the transducer before concentration estimates can be made. These techniques are therefore inherently imprecise and/or of limited applicability across a range of applications.

There remains a need for improved techniques for using ultrasound images to measure particle concentration.

SUMMARY

The systems and methods of the present disclosure are directed to ultrasound-based concentration measurement techniques in which both scatterer count and an image volume are measured concurrently to provide absolute concentration measurements. In particular, through the techniques of the present disclosure, the effective thickness of an ultrasound beam can be determined based on the spreading of individual scatterers within ultrasound images. Based on the effective thickness of the ultrasound beam, the volume of the image and, thus, the absolute concentration of particles in the image can be determined directly, without the need for estimation, approximation, or use of a reference sample.

In one aspect, a method includes acquiring an ultrasound image (e.g., a B-mode ultrasound image) of a medium with an ultrasound transducer, wherein the ultrasound image includes at least a portion of a two-dimensional image obtained from the ultrasound transducer and wherein the medium contains a number of scatterers, determining an effective volume of the ultrasound image in which one or more of the number of scatterers in the medium produce an echo detectable within the two-dimensional image, counting the scatterers in the ultrasound image, and, based on the counted scatterers and the effective volume of the ultrasound image, determining an absolute concentration of the scatterers in the medium.

In some implementations, determining the absolute concentration of the scatterers in the medium includes determining the absolute concentration of the scatterers without contacting the medium.

In certain implementations, determining the effective volume of the ultrasound image is based on echogenicity of the scatterers and attenuation of the medium.

In some implementations, determining the effective volume of the ultrasound image is based on a ratio of an elevational beam profile to a lateral beam profile. In addition, or in the alternative, an elevational axis is perpendicular to the two-dimensional ultrasound image and determining the effective volume of the two-dimensional ultrasound image can include determining an effective beam thickness along an elevational axis of the ultrasound image. For example, determining the effective beam thickness can include slicing the ultrasound image into a plurality of slices along an axial axis of the ultrasound image, determining an effective slice thickness for each slice, and, based on the effective slice thickness, determining an effective slice volume. Determining the effective slice thickness can be, in certain implementations, based on the extent to which the counted scatterers, detected as echoes in the respective slice, deviate from an axis of the ultrasound transducer. In certain implementations, determining the absolute concentration of the scatterers in the medium includes determining the absolute concentration of the scatterers in each slice. The absolute concentration of the scatterers in each slice can be, for example, the ratio of the counted scatterers in the slice to the volume of the slice, the volume of the slice based on the lateral width of the image, axial length of the slice, and the effective thickness of the slice. In some implementations, determining the absolute concentration of the scatterers in the medium further, or in the alternative, includes averaging at least some of the absolute slice concentrations. For example, averaging at least some of the absolute slice concentrations can include averaging the absolute slice concentrations corresponding to a predetermined cutoff based on an amplitude range of echoes.

In certain implementations, the method further includes selecting scatterers of interest from the ultrasound image. Selecting the scatterers of interest can include, for example, classifying scatterers in the ultrasound image into different particle types, wherein the steps of counting the scatterers, determining the effective volume, and determining an absolute concentration of scatterers are performed for each classified particle type. Additionally, or alternatively, selecting the scatterers of interest can include spectral analysis of echoes in the ultrasound image. As an example, such spectral analysis of echoes in the ultrasound image can be based on observed peak frequency in backscatter coefficient of the echoes in the ultrasound image.

In some implementations, acquiring the ultrasound image includes acquiring the ultrasound image from a radially symmetric ultrasound transducer. In addition, or in the alternative, acquiring the ultrasound image can include acquiring the ultrasound image from a linear array transducer.

In certain implementations, the absolute concentration of the scatterers is less than about 200 particles/μL.

In some implementations, the detectable echoes in the ultrasound image correspond to scatterers that are about 15 μm or less.

In certain implementations, the detectable echoes in the ultrasound image correspond to T-cells.

In another aspect, a method includes adding particles to a biological sample of cells in a medium, the cells having an affinity for the added particles, acquiring a two-dimensional ultrasound image, obtained by an ultrasound transducer, of the biological sample with the added particles, counting, in the ultrasound image, cells with changed acoustic properties in the presence of the added particles, determining an effective volume of at least a portion of the ultrasound image, and based on the counted cells with changed acoustic properties and the effective volume of the ultrasound image, determining an absolute concentration of the cells with changed acoustic properties in the biological sample. The added particles can be, for example, of a known and detectable size. As an additional or alternative example, the added particles can be polystyrene microspheres. In certain implementations, the cells with changed acoustic properties are bound to the added particles. Additionally, or alternatively, the cells can be T-cells.

In another aspect, a method includes acquiring a two-dimensional ultrasound image (e.g., a B-mode ultrasound image), obtained by an ultrasound transducer, of a medium containing a number of scatterers, determining a backscatter coefficient for echoes in the ultrasound image, based on a peak frequency of the backscatter coefficient of the echoes, classifying each echo as a respective scatterer type, and determining a particle count of a classified scatterer type based on a number of peaks at the peak frequency associated with the classified scatterer type.

In some implementations, classifying each echo as a corresponding scatterer type includes classifying each echo as one of a plurality of scatterer types. Determining the particle count of the classified scatter type can include, for example, determining a particle count for each of the plurality of scatterer types. Additionally, or alternatively, acquiring the two-dimensional ultrasound image can include acquiring a set of two-dimensional ultrasound frames and determining the particle count for each of the plurality of scatterer types for the set of two-dimensional ultrasound frames.

In still another aspect, a system includes an ultrasound transducer having an adjustable beam shape, and a controller including one or more processors and a non-transitory, computer-readable storage medium having computer executable instructions for causing the one or more processors to receive an expected concentration of a sample, adjust the beam shape based on the received expected concentration, acquire a two-dimensional ultrasound image from the transducer, with the adjusted beam shape, of a medium containing a number of scatterers, count the scatterers in the ultrasound image, determine an effective volume of at least a portion of the ultrasound image, and, based on the counted scatterers and the effective volume of the ultrasound image, determine an absolute concentration of the scatterers in the medium.

In some implementations, the ultrasound transducer can include a beam width adjustable in an elevational direction. For example, the ultrasound transducer can include a plurality of rows of piezoelectric elements in an elevational direction, and a beam width of the ultrasound transducer is adjustable in the elevational direction by activating or deactivating one or more of the rows of piezoelectric elements.

Implementations can include one or more of the following advantages.

In certain implementations, the absolute concentration of scatterers is determined from an acquired ultrasound image. Thus, as compared to methods that require destruction of the sample, the determination of absolute concentration of scatterers from an acquired ultrasound image can facilitate preservation of the sample (e.g., for use in other types of diagnostic testing). Additionally, or alternatively, as compared to methods that require extraction of the sample from the body through an invasive procedure, the determination of absolute concentration of scatterers from an acquired ultrasound image can avoid an invasive procedure that would otherwise be required to extract the sample and, thus, can avoid the risk of infection and/or complication associated with such invasive procedures.

In some implementations, the absolute concentration of scatterers in a medium is determined based on the effective volume of an ultrasound image of the scatterers. This facilitates determination of the absolute concentration of the scatterers without the need for calibration of an imaging system to a particular sample and, additionally or alternatively, without the need for a reference suspension of known concentration. Thus, as compared to methods of determining concentration that require calibration and/or reference materials, the determination of absolute concentration of scatterers based on the effective volume of the ultrasound image can be applied across a wide range of clinical and/or laboratory applications with only characterization of the ultrasound imaging system required. For example, determining absolute concentration of scatterers based on the effective volume of the ultrasound image accounts for variations in scatterer echogenicity, scatterer size, and/or attenuation in the medium in which the scatterers are suspended.

BRIEF DESCRIPTION OF THE FIGURES

FIG. 17 is a graph of concentration measurement results from ultrasound images compared to concentration measurements from a hemocytometer for four polydispersed samples of 10 μm and 15 μm polystyrene microspheres suspended in distilled water, with the concentration of the 15 μm polystyrene microspheres held constant while the concentrations of the 10 μm polystyrene microspheres varied across the samples.

Like reference symbols in the various drawings indicate like elements.

DETAILED DESCRIPTION

The embodiments will now be described more fully hereinafter with reference to the accompanying figures, in which preferred embodiments are shown. The foregoing may, however, be embodied in many different forms and should not be construed as limited to the illustrated embodiments set forth herein.

All documents mentioned herein are hereby incorporated by reference in their entirety. References to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," "substantially" or the like, when accompanying a numerical value, are to be construed as including any deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the disclosed embodiments.

In the following description, it is understood that terms such as "first," "second," "top," "bottom," "above," "below," "up," "down," and the like, are words of convenience and are not to be construed as limiting terms unless specifically stated.

Figure 1:
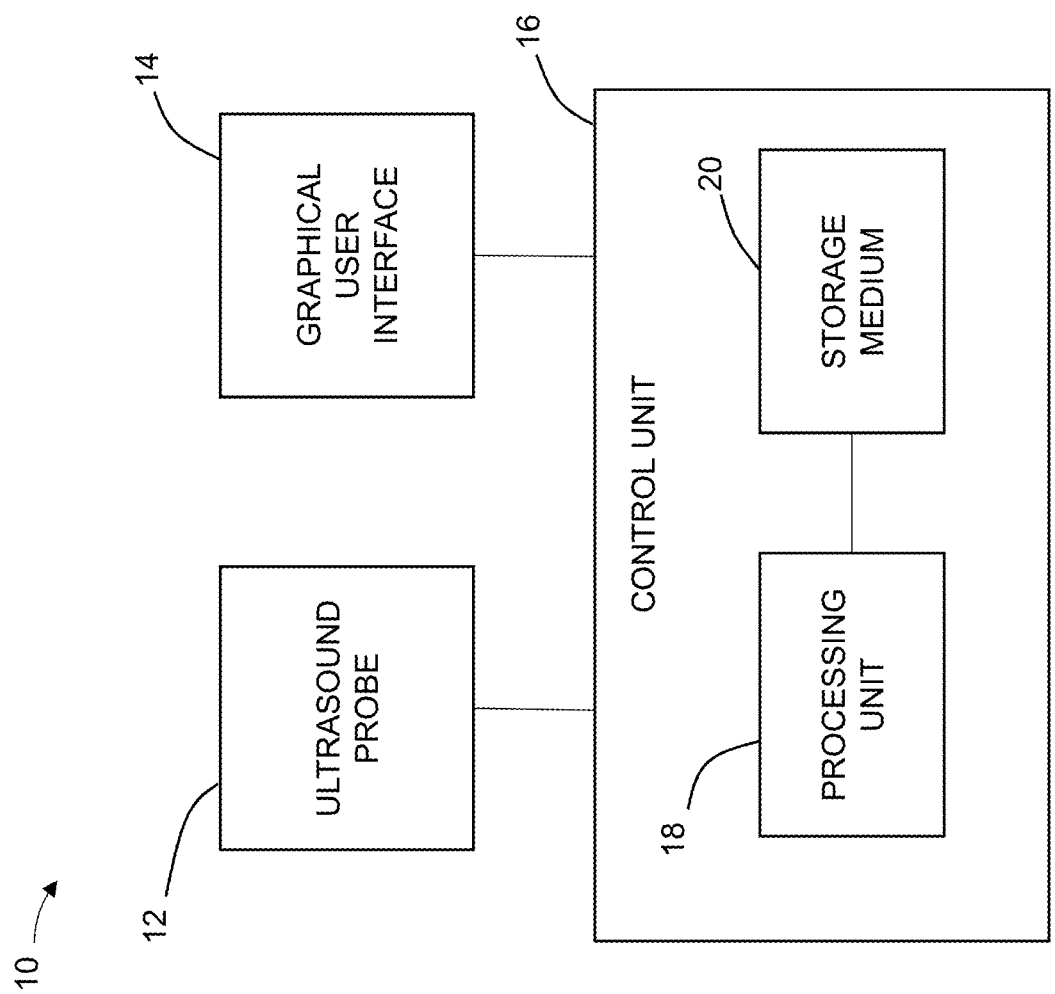
FIG. 1 is a schematic representation of an ultrasound system including an ultrasound probe, a graphical user interface, and a control unit.
Figure 2:
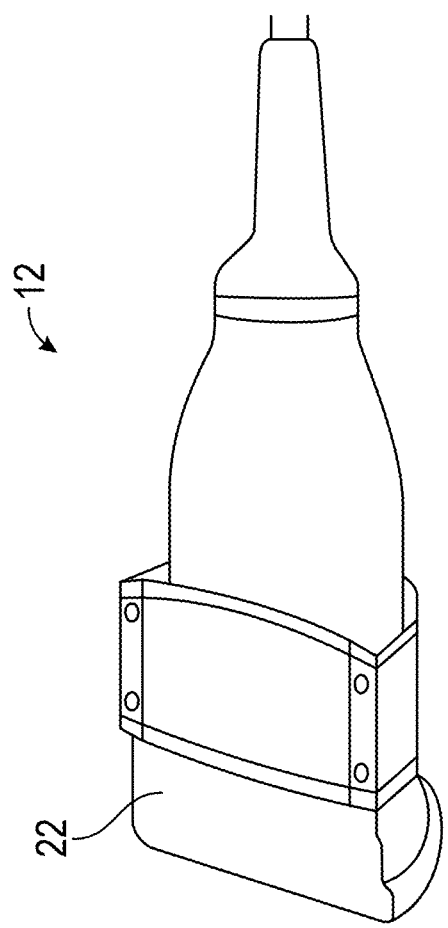
FIG. 2 is a perspective view of an ultrasound probe of FIG. 1.
Figure 3:
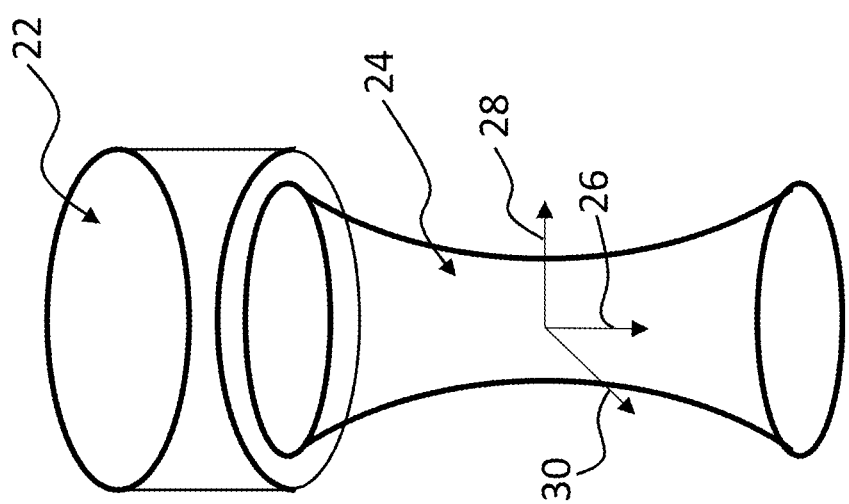
FIG. 3 is a schematic representation of an ultrasound transducer of the ultrasound probe of FIG. 1 producing a beam.
Figure 4:
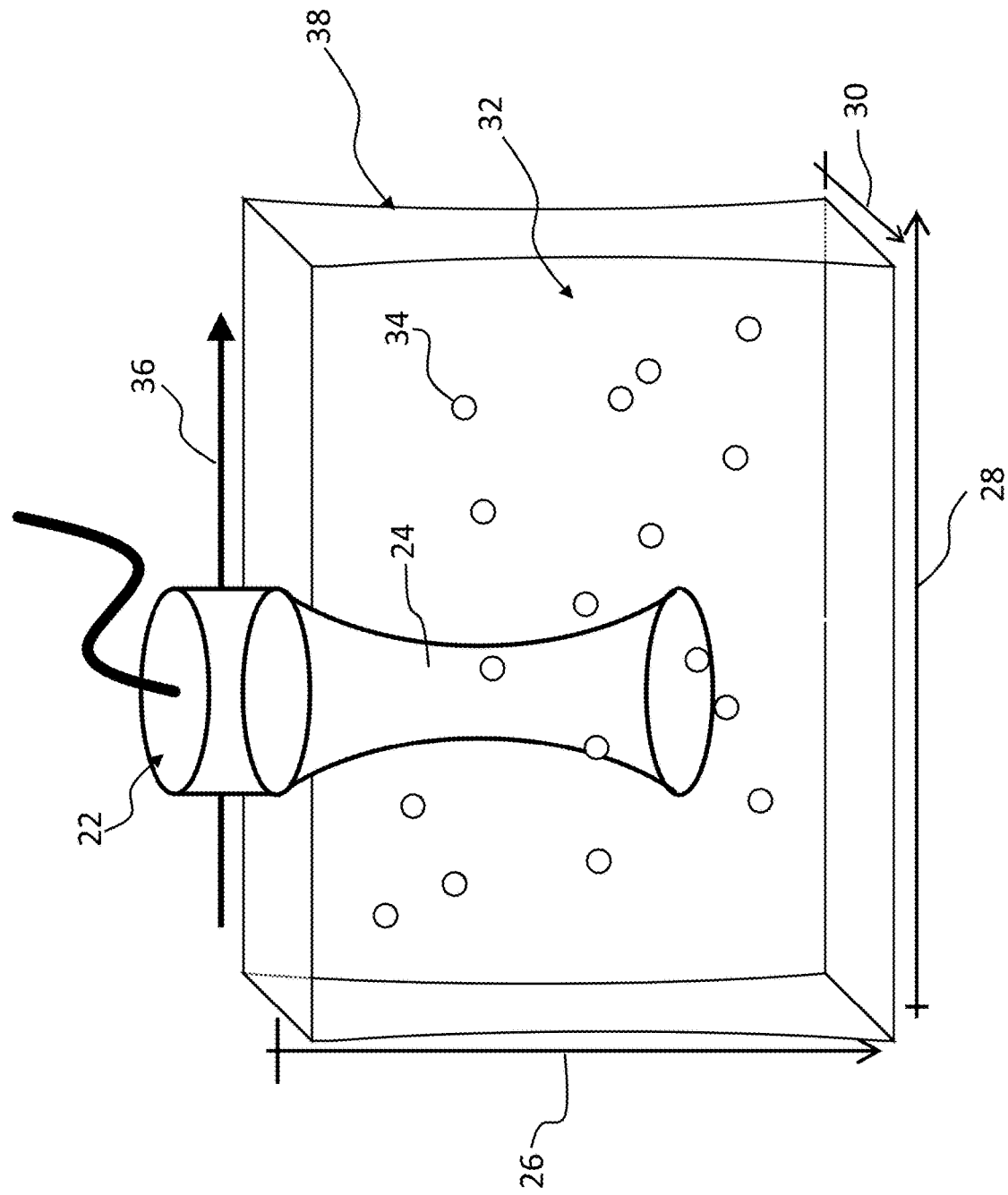
FIG. 4 is a schematic representation of an ultrasound scan of a sample.

Referring to FIGS. 1 and 2, an ultrasound system 10 includes an ultrasound probe 12, a graphical user interface 14, and a control unit 16 in communication with the ultrasound probe 12 and the graphical user interface 14. The control unit 16 includes a processing unit 18 and a non-transitory, computer-readable storage medium 20 storing instructions executed by one or more processors of the processing unit 18. In use, the probe 12 can be brought into contact with skin of a patient and/or with a container of a sample or any other scanned object or target, and the control unit 16 can control the probe 12 to generate ultrasound signals into the target. The returning ultrasound signals can be detected by the probe 12 and directed to the control unit 16, where the returning ultrasound signals can be processed into a two-dimensional ultrasound image of a transverse plane through the target that may be displayed on the graphical user interface 14.

As described in greater detail below, the control unit 16 determines the effective thickness of the ultrasound beam into the plane of the two-dimensional ultrasound image to arrive at an effective volume that accounts for the properties of the medium being imaged, the interface between an ultrasound transducer and the scanned object, and a variety of other factors. As also described in greater detail below, the control unit 16 may count scatterers in the two-dimensional ultrasound image and, based on this particle count and the effective volume, determine the absolute concentration of the particles in the medium. As used herein, the term "absolute concentration" refers to a concentration of particles that is determined based on counting discrete particles within a scan of known or calculated volume, which as disclosed herein may be determined without reference to a suspension of particles of known concentration or any other reference or control sample. Unless otherwise indicated, the terms "scatterers" and "particles" are used interchangeably herein, given that, in the present disclosure, the particles in the medium being imaged scatter the incident ultrasound waves.

The ultrasound probe 12 can be of any known type or construction including, for example, an off-the-shelf ultrasound probe for medical imaging. As described in greater detail below, the methods of the present disclosure account for variations (e.g., in size and shape) in different types of probes and, therefore, can be implemented without calibration to a sample of a known concentration.

The ultrasound probe 12 includes an ultrasound transducer 22. The construction of suitable ultrasound transducers is generally well known. In some implementations, an ultrasound transducer includes piezoelectric crystals to generate ultrasound waves that are directed into the imaged volume and/or detect ultrasound waves (e.g., radio frequency (RF) echo data) returning from the imaged volume. Any suitable arrangement for transmitting and/or receiving ultrasound may be used as the ultrasound transducer 22 in the embodiments described herein.

The graphical user interface 14 can be a graphical display of any known type or construction (e.g., a computer monitor associated with a desktop computer and/or a laptop computer) and can be in wired or wireless communication with the control unit 16. Additionally, or alternatively, the graphical user interface 14 can be integrated into the ultrasound probe 12.

In use, the two-dimensional ultrasound image based on data obtained by the ultrasound probe 12 can be displayed on the graphical user interface 14 using known techniques. For example, multiple two-dimensional ultrasound images can be displayed on the graphical user interface 14 as the two-dimensional ultrasound images are received in real time. In certain implementations, one or more input devices (e.g., a keyboard and/or mouse) in communication with the ultrasound system 10 can be used to manipulate the two-dimensional ultrasound image displayed on the graphical user interface 14.

The storage medium 20 may store instructions executed by one or more processors of the processing unit 18 to perform the methods described herein. The storage medium 20 may also or instead store ultrasound data from the ultrasound transducer 22 acquired during an ultrasound scan, as well as any intermediate representations of scan data, processed results, and so forth. The storage medium 20 can be integrally built into the ultrasound probe 12 to operate as a standalone device. Additionally, or alternatively, the storage medium 20 may include external storage, such as in a desktop computer, network-attached storage, or other device with suitable storage capacity that is locally or remotely coupled to the control unit 16 or ultrasound probe 12. In one aspect, data may be wirelessly transmitted from the ultrasound probe 12 to the storage medium 20 such that the ultrasound probe 12 can be operated wirelessly. Wired communications may also or instead be used to transmit data from the ultrasound probe 12 to the storage medium 20.

The processing unit 18 may be a local or remote computer provided for pre-scan configuration and post-scan or in-scan processing of data. In general, the processing unit 18 and/or a related computing device may have sufficient processing capability to perform the quantitative processing described herein. For example, the processing unit 18 may have sufficient processing capability to control the transmission of ultrasound waves from the ultrasound transducer 22 of the ultrasound probe 12 into the medium and to form an ultrasound image based on radio frequency echo data (e.g., B-mode data) received from the medium via the ultrasound transducer 22. The processing unit 18 may further have sufficient processing capability to process the resulting B-mode image of the medium to provide a concentration of scatterers in the medium, with the concentration of the particles in the medium being based on a count of scatterers in a two-dimensional ultrasound image and on the effective volume of the two-dimensional ultrasound image.

In one aspect, the graphical user interface 14 and the control unit 16, including the processing unit 18 and the storage medium 20, are a desktop or laptop computer. In another aspect, these components may be separate, or there may exist some combination of these. For example, the graphical user interface 14 may be a supplemental display provided for use by a doctor or technician during an ultrasound scan. The storage medium 20 may include a network-attached storage device or the like that logs ultrasound images and other acquisition state data.

In general, the methods described herein use B-mode images to measure absolute concentration of particles in suspension for low concentration samples. The methods of the present disclosure are based on detecting individual particles in the image to acquire a particle count, and using the characteristics of the echoes to determine the volume analyzed by the image. It should be appreciated that the presently disclosed methods are image-based and, therefore, non-invasive and non-destructive to the sample, offering advantages over particle counting methods such as using a hemocytometer, using a Coulter counter, and flow cytometry-based concentration measurements. Further, the presently disclosed methods can be carried out without prior characterization of the sample, thus offering advantages over other ultrasound-based techniques (e.g., techniques requiring calibration to a suspension of known particle concentration).

Referring now to FIGS. 1-4, the ultrasound system 10 is an exemplary system for determining absolute concentration of materials with low scatter concentration according to the methods described herein. The ultrasound transducer 22 of the ultrasound probe 12 produces a beam 24 having dimensions along an axial axis 26, a lateral axis 28, and an elevational axis 30. The axial axis 26 and the lateral axis 28 are in the plane of the ultrasound image produced by the ultrasound transducer 22, and the elevational axis 30 is perpendicular to the ultrasound image. The beam is shown as being radially symmetric along the lateral axis 28 and the elevational axis 30. However, the beam shape can, additionally or alternatively, be asymmetric. As described in greater detail below, the methods described herein are applicable to implementations in which the dimensions of the beam 24 are asymmetric along the lateral axis 28 and the elevational axis 30.

The ultrasound probe 12 can be positioned such that the beam 24 produced by the ultrasound transducer 22 is directed toward a medium 32 containing scatterers 34. The ultrasound probe 12 can be moved along a scan direction 36 such that the ultrasound transducer 22 directs ultrasound waves into the medium and receives reflections of the ultrasound waves (RF echo data) as the ultrasound probe 12 moves in the scan direction 36, resulting in a scanned volume 38. The RF echo data received by the ultrasound transducer 22 can be communicated to the processing unit 18 for formation into a two-dimensional ultrasound image (e.g., a B-mode image) of the scanned volume 38.

Figure 5:
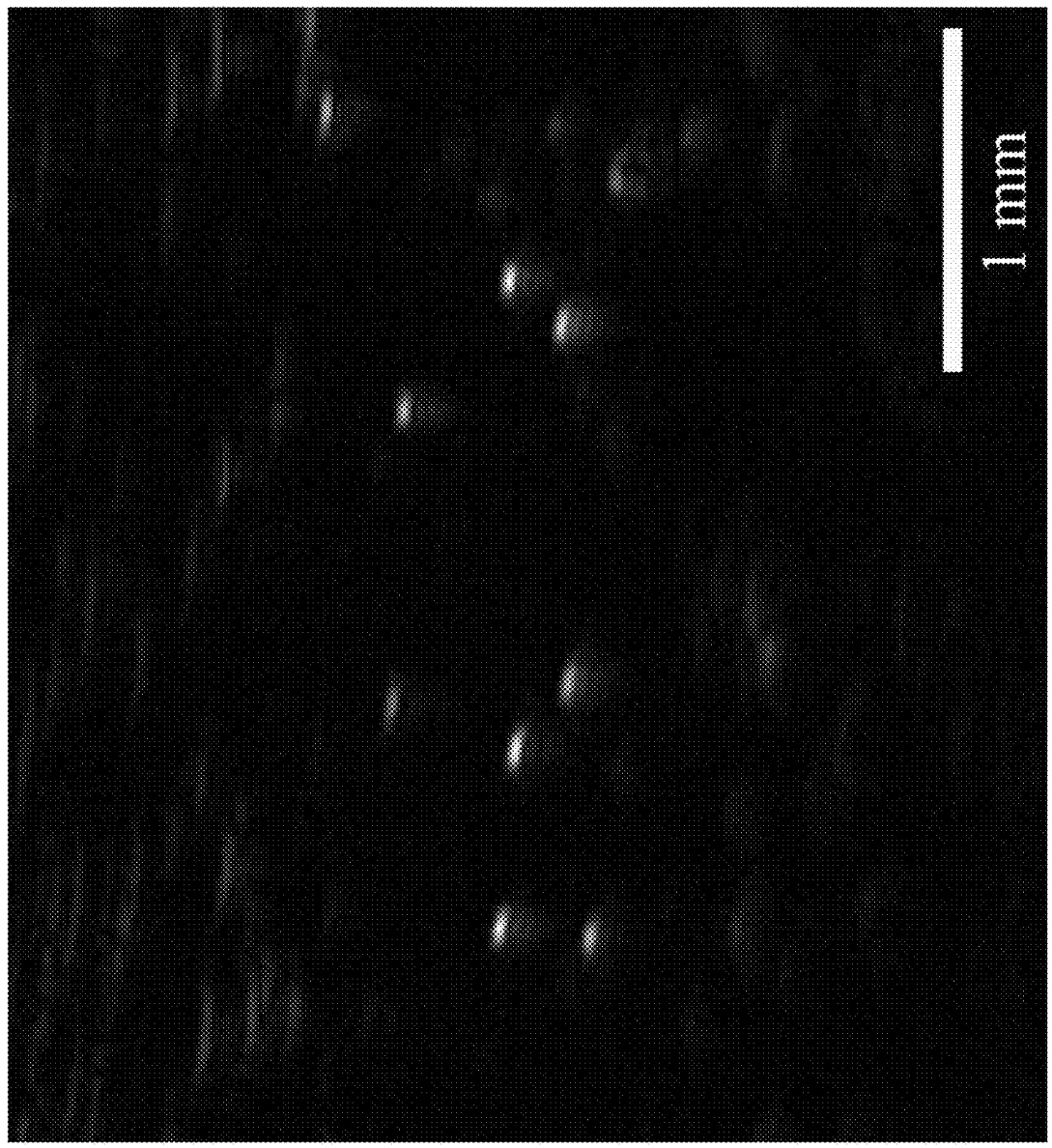
FIG. 5 is a B-mode ultrasound image, acquired using the ultrasound system of FIG. 1, and showing individual particles of 15 μm polystyrene microspheres suspended in distilled water at a concentration of 50 particles/μL.

Referring now to FIG. 5, a B-mode ultrasound image is shown. The image corresponds to a scan of 15 μm polystyrene microspheres suspended in distilled water with a concentration of 50 particles/μL. The material scanned has low scatter concentration which, on average, includes a concentration less than or equal to one scatterer per resolution cell. Because of this low scatterer concentration, individual scatterers can be distinguished in the respective B-mode ultrasound images.

Referring now to FIGS. 1-5, given the two-dimensional ultrasound image of the sample, the number of scatterers 34 visible in the image can be determined using any suitable image processing technique including, by way of non-limiting example, the techniques described below. To determine the concentration of the scatterers 34 in the medium 32, the scanned volume 38 corresponding to the two-dimensional ultrasound image must also be determined. The dimensions of the scanned volume 38 along the axial axis 26 and the lateral axis 28 can be characterized directly from the two-dimensional ultrasound image. The two-dimensional ultrasound image has a nonzero thickness because the beam 24 has a nonzero width along the elevational axis 30. However, the effective thickness of the image, which is the width of the beam 24 along the elevational axis 30, depends not only on the characteristics of the beam 24, but also on the characteristics of the scatterers 34 and the medium 32. Thus, the effective thickness of the scanned volume 38 along the elevational axis 30 generally does not correspond to a width of the beam 24 calculated from beam characteristics alone.

As used herein, the term effective thickness refers to the dimension of the scanned volume 38 and, thus to the effective width of the beam 24, along the elevational axis 30. More generally, as used herein, the term "effective" conveys that the thickness is referring to more than a single quantity defined by beam characteristics alone and, instead, is a quantity that depends on the entire setup of the measurement, including the imaging system and the sample. In particular, the effective thickness is the extent to which a scatterer can be detected along the elevational axis 30. Thus, the corresponding effective volume of the two-dimensional ultrasound image is a volume of the two-dimensional ultrasound image calculated using the effective thickness, along with the respective known dimensions along the axial axis 26 and the lateral axis 28. This effective volume generally corresponds to the volume within the ultrasound beam in which one or more scatterers 34 in the medium 32 produce an echo detectable within the two-dimensional ultrasound image. It should be appreciated that characterizing the effective volume captures an aggregate effect of the interaction between the beam 24 produced by the ultrasound transducer 22 and the sample, without having to characterize each separately.

Figure 6:
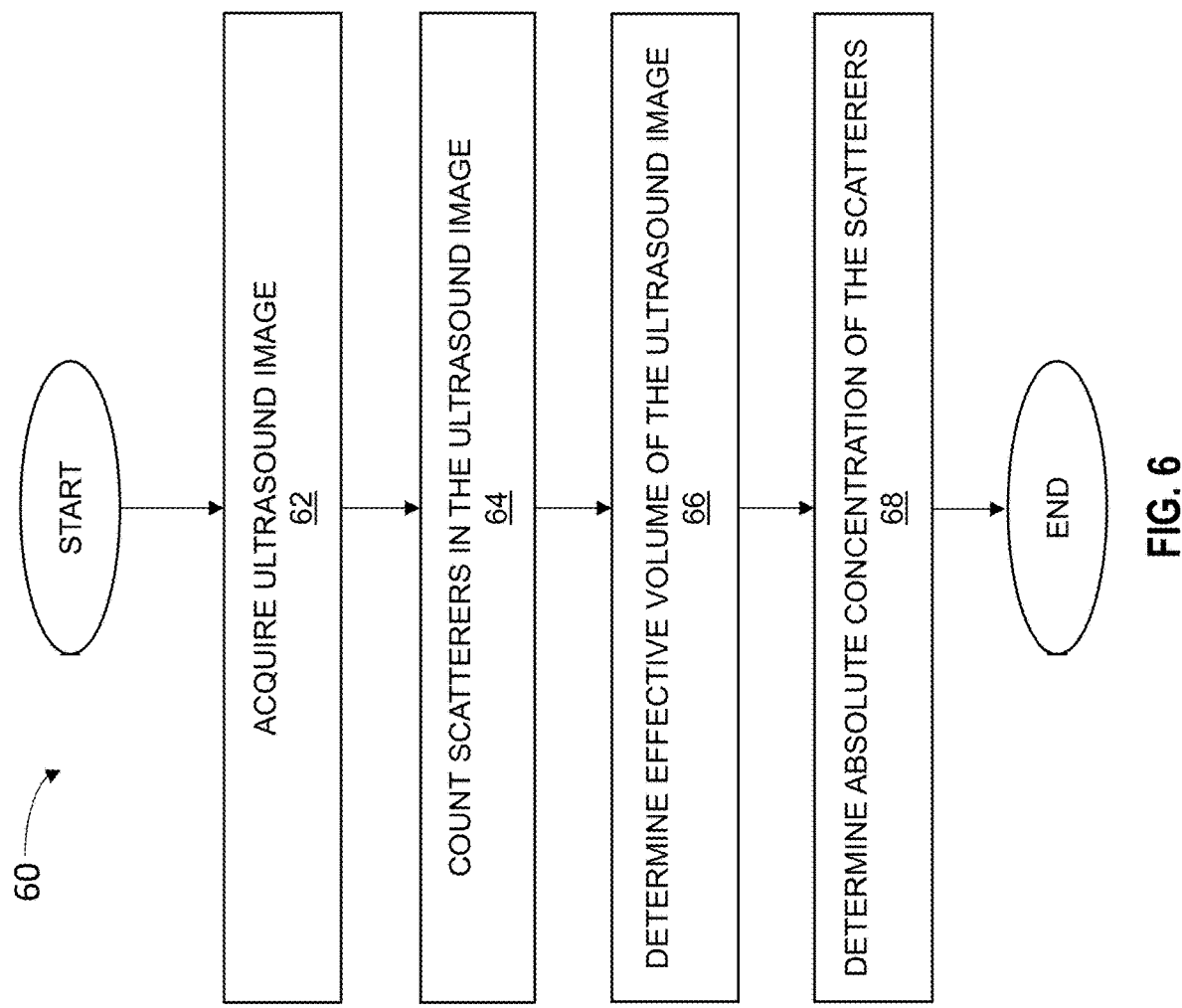
FIG. 6 is a flowchart of an exemplary method of determining absolute concentration of scatterers from an ultrasound image.

Referring now to FIG. 6, an exemplary method 60 of determining an absolute concentration of scatterers from an ultrasound image using, for example the ultrasound system 10 (FIG. 1), includes acquiring 62 an ultrasound image of a medium with an ultrasound transducer, counting 64 scatterers in the ultrasound image, determining 66 an effective volume of the ultrasound image, and determining 68 the absolute concentration of the scatterers in the medium. As described in greater detail below, the determined 68 absolute concentration of the scatterers in the medium can be based on the counted 64 scatterers and the determined 68 effective volume of the ultrasound image. As also described in greater detail below, because the determined 68 absolute concentration of the scatterers in the medium cam be derived directly from an ultrasound image, the exemplary method 60 can be used on different sample types without the need for a calibration or a reference measurement.

As used herein, acquiring 62 an ultrasound image of a medium includes acquiring a set of two-dimensional ultrasound frames. Additionally, acquiring 62 an ultrasound image of a medium using an ultrasound transducer can include acquiring high frequency B-mode images with any of various different types of ultrasound transducers. For example, acquiring 62 the ultrasound image can include acquiring high frequency B-mode images using a mechanically scanned single element transducer (e.g., with a spherically focused single element disk transducer). Additionally, or alternatively, acquiring 62 the ultrasound image can include acquiring high frequency B-mode images using an ultrasound imaging system including linear arrays. More generally, as described in greater detail below, the methods described herein may account for single and multi-transducer geometries and arrays.

Further, acquiring 62 an ultrasound image of a medium using an ultrasound transducer includes acquiring 62 the ultrasound image in vivo or in vitro. That is, acquiring 62 the ultrasound image includes placing an ultrasound transducer in proximity to a patient's skin, directing ultrasound energy toward a medium within the patient's body, and acquiring the ultrasound image in a conventional manner. For in vitro measurements, acquiring 62 the ultrasound image includes placing an ultrasound transducer in proximity to a medium, directing ultrasound energy toward the medium, and similarly acquiring the ultrasound image in a conventional manner. In each instance, therefore, acquiring 62 the ultrasound image is non-invasive and does not contaminate the medium being analyzed.

Figure 7:
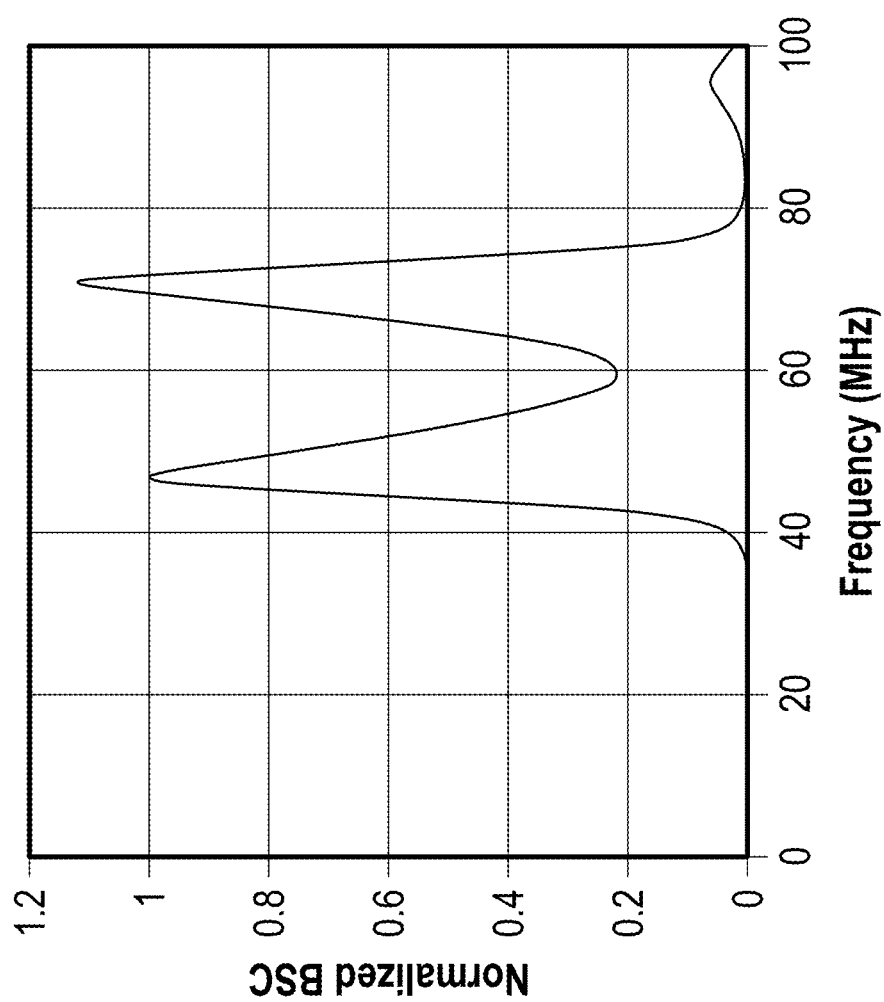
FIG. 7 is an exemplary graph of normalized backscatter coefficient as a function of frequency for a detected echo from a B-mode ultrasound image of an exemplary 15 μm polystyrene microsphere suspension having a concentration of 25 particles/μL.
Figure 8:
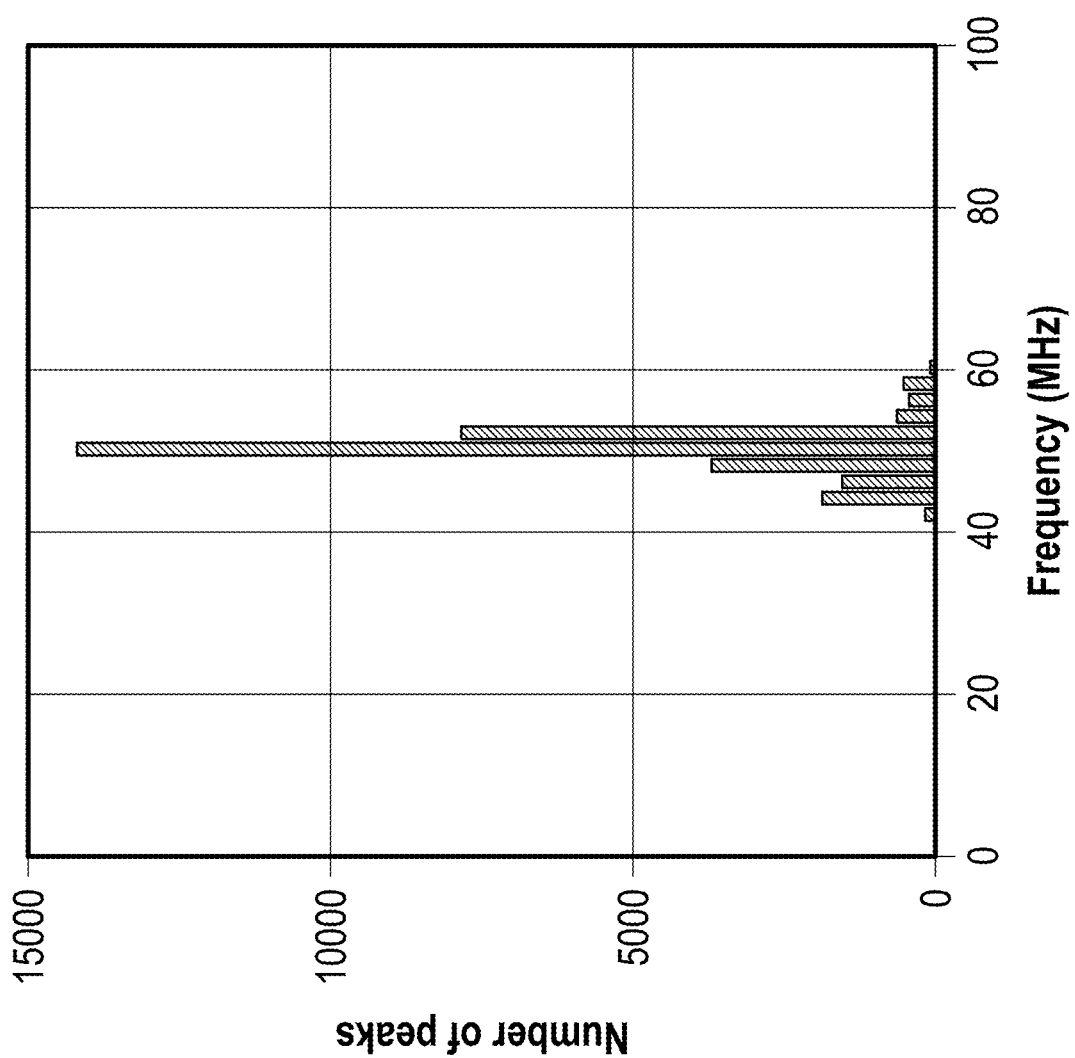
FIG. 8 is a histogram of peak frequency in backscatter coefficient for each detected echo in all measured frames of the B-mode ultrasound image of the exemplary 15 μm polystyrene microsphere suspension having a concentration of 25 particles/μL.

Referring now to FIGS. 6-8, counting 64 scatterers can be performed on measured frames (e.g., all measured frames) of the acquired 62 ultrasound image. To improve detection accuracy of counting 64 scatterers, noise reduction can be performed by using a median filter and a 2D Gaussian filter.

Particle detection is performed based on template matching with a 2D Gaussian as the template. Additionally, or alternatively, another type of template can be used. For example, a template may be based on some general prior knowledge about the scatters and/or a template may be extracted from training data. As described in greater detail below, counting 64 scatterers can include analysis of envelope-detected images by locating the echoes from individual particles. For the sake of clarity of explanation, exemplary methods of counting 64 scatterers are described with respect to data acquired from a 15 μm polystyrene microsphere sample (25 particles/μL) using a mechanically scanned single element transducer imaging system (MS). It should be appreciated, however, that these exemplary methods of counting 64 scatterers can be additionally, or alternatively, applicable to other types of particles, different particle sizes, different particle concentrations, and/or different transducer imaging systems without departing from the scope of the present disclosure.

In one useful embodiment, the MS includes a 75 MHz spherically focused single element disk transducer with 6.35 mm diameter and 12.7 mm focal distance (f-number of 2) (such as a V3320 high frequency transducer, available from Olympus NDT, Waltham, Mass.) that is linearly scanned. The −6 dB bandwidth of the transducer is 81%. The linear scanning is performed with a 3-axis scanning stage driven with stepper motors. The motors use a low-noise linear stepper motor driver (such as CLD low-noise linear stepper motor driver, available from Phytron Inc., Williston, Vt.) to reduce coupling of the electrical noise of the motor into the ultrasound signal. The scanning achieves lateral stepping resolution of 10 μm. Ultrasound imaging is performed with a square wave-based high frequency pulser-receiver (P/R) (such as a UT340 square wave-based high frequency pulser-receiver, available from UTEX Scientific Instruments, Ontario, Canada) and the received signal is digitized with a PicoScope 5444b (available from Pico Technology, Cambridgeshire, United Kingdom) at a sampling rate of 500 Msps at 12-bit resolution. Images are acquired in both scanning directions. An image may be constructed by stacking 350 scan lines spaced by 10 μm, resulting in an image width of 3.5 mm. While this is a useful embodiment, it will be understood that other configurations and components may be used without departing from the scope and spirit of this disclosure.

In certain implementations, counting 64 scatterers further includes spectral analysis of echoes in the ultrasound image. As an example, spectral analysis of echoes in the ultrasound image can include backscatter coefficient (BSC) analysis, in which the BSC along the axial direction can be calculated by averaging the magnitude of the Fourier transforms of each scan line and dividing by the flat reflector measurement, which is expressed as a normalized parameter as follows:

$$\text{Normalized } BSC = \text{Normalize}\left(\left|\frac{\frac{1}{N}\sum_{i=1}^{N}H_i(f)}{H_{flat}(f)}\right|^2\right) \quad \text{(Eq. 1)}$$

where,

N is the number of scan lines in the extracted RF data, $H_i(f)$ is the Fourier transform of the $i^{th}$ scan line, and $H_{flat}(f)$ is the Fourier transform of the flat reflector measurement.

The normalized BSC for a given echo, calculated according to Eq. 1, is shown in FIG. 7. The frequency of the first peak in the normalized BSC can be used to classify the particle type. Thus, counting 64 can include repeating, for each detected echo in a plurality of measured frames (e.g., all measured frames) of the acquired 62 ultrasound image, the determination of the first peak in the normalized BSC. As shown in FIG. 8, for example, counting 64 can include determining the number of peaks at each frequency. In general, in monodispersed samples, the classification based on peak frequencies can be used to select only the particles of interest and remove any echoes from unwanted scatterers such as microbubbles or other impurities in the sample. In polydispersed samples, as described in greater detail below, the peak frequencies can advantageously be exploited to classify the scatterers such that the concentration of each type can be calculated.

Figure 9:
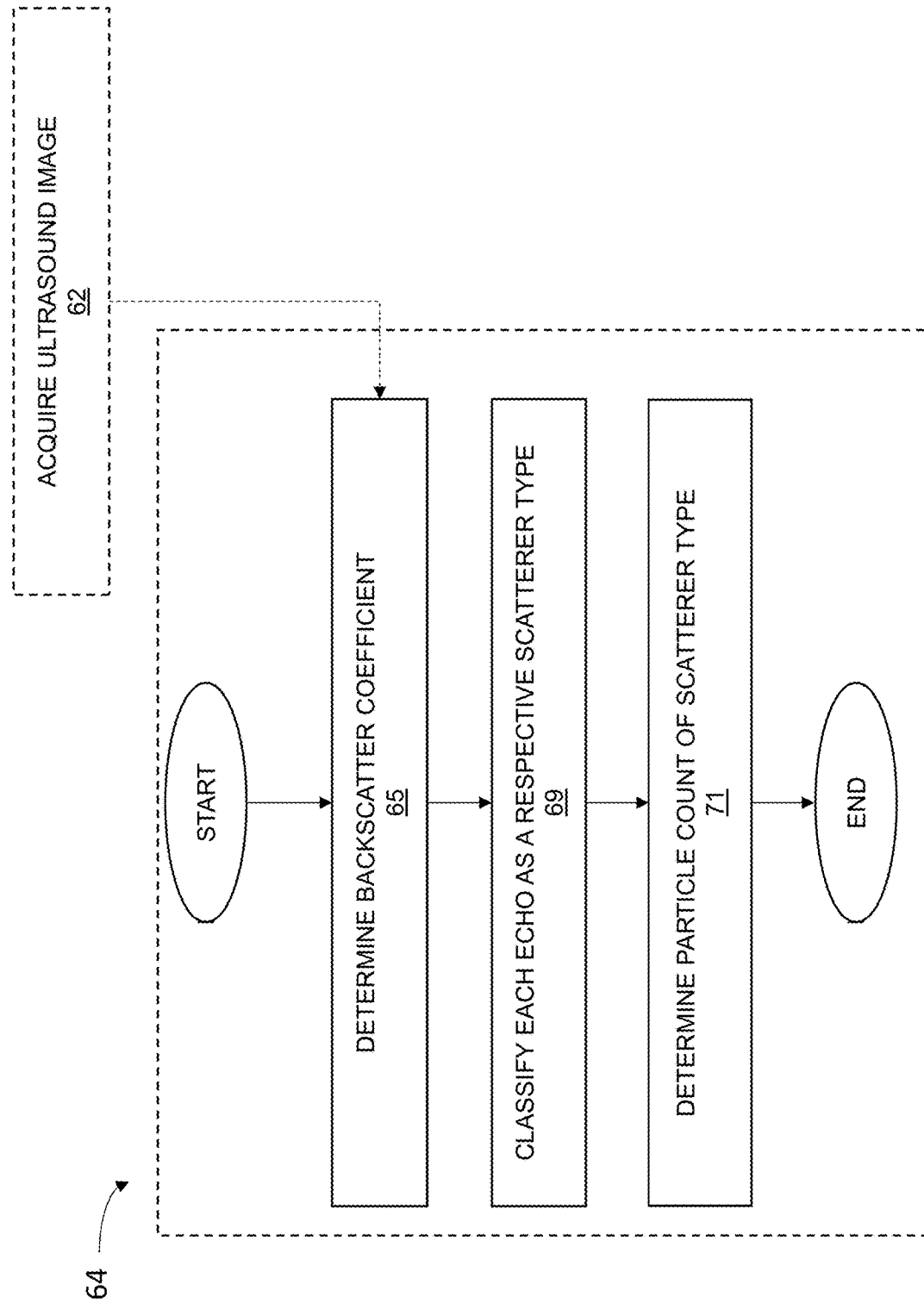
FIG. 9 is a flowchart of an exemplary method of counting scatterers in an acquired ultrasound image.

Referring now to FIG. 9, an exemplary method of counting 64 scatterers based on the acquired 62 two-dimensional ultrasound image includes determining 65 a backscatter coefficient for echoes in the ultrasound image, classifying 69 each echo as a respective scatterer type, and determining 71 a particle count of a classified scatterer type. Classifying 69 each echo as a respective scatterer type can be based on a peak frequency of the backscatter coefficient of echoes (e.g., echoes with the same peak frequency are classified as the same scatterer type) according to any of the methods described herein. Determining 71 the particle count of a classified scatterer type, then, can be based on the number of peaks at the peak frequency associated with the classified scatterer type according to any of the methods described herein. The exemplary method of counting 64 scatterers can be repeated for each of a plurality of scatterer types that are classified 69. Further, the determination 71 of the particle count for each of the plurality of scatterer types can be repeated for a set of multiple two-dimensional ultrasound frames of the acquired 62 ultrasound image.

Referring now to FIG. 6 and FIGS. 10A-10C, determining 66 the effective volume of the acquired 62 ultrasound image is generally based on the relationship between echo amplitude and elevational position of the scatterer. For the sake of clarity of explanation, the relation between echo amplitude and elevational position of scatterers and, thus, exemplary methods of determining 66 the effective volume of the acquired 62 ultrasound image are explained with continued reference to the B-mode ultrasound of the exemplary 15 μm polystyrene microsphere suspension (25 particles/μL) discussed above.

Determining 66 the effective volume of the acquired 62 ultrasound image can include, for each echo in a B-mode ultrasound image of a sample, extracting the corresponding location in the two-dimensional RF data of the acquired 62 ultrasound image. The echo envelope can be fitted, for example, to a 2D Gaussian to estimate lateral standard deviation and amplitude of the echo envelope, which can be used to characterize a respective scatterer spread function (SSF) of the echo envelope. The axial and lateral positions of the scatterer can be determined from the location of the centroid of the Gaussian fitting.

Figure 10A:
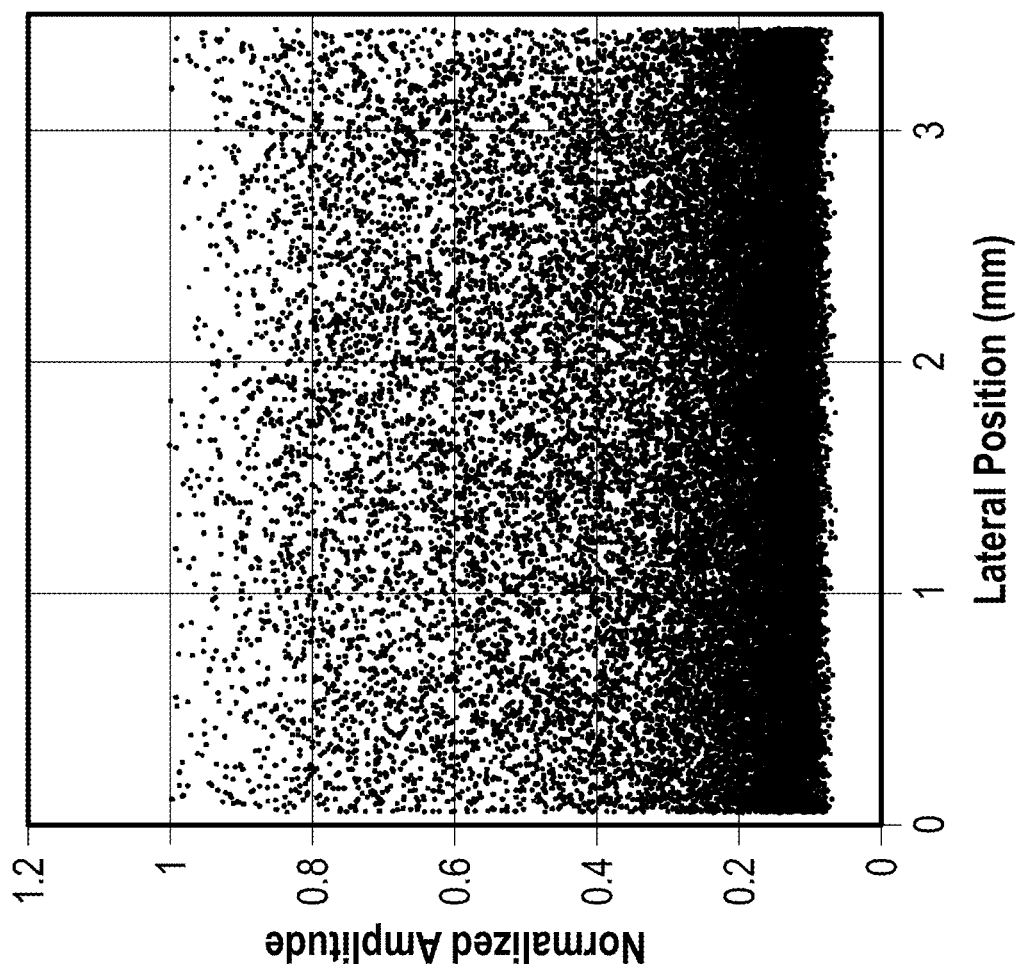
FIG. 10A is a scatter plot of normalized echo amplitude as a function of lateral position for each detected echo in all measured frames of the B-mode ultrasound image of the exemplary 15 μm polystyrene microsphere suspension having a concentration of 25 particles/μL.
Figure 10B:
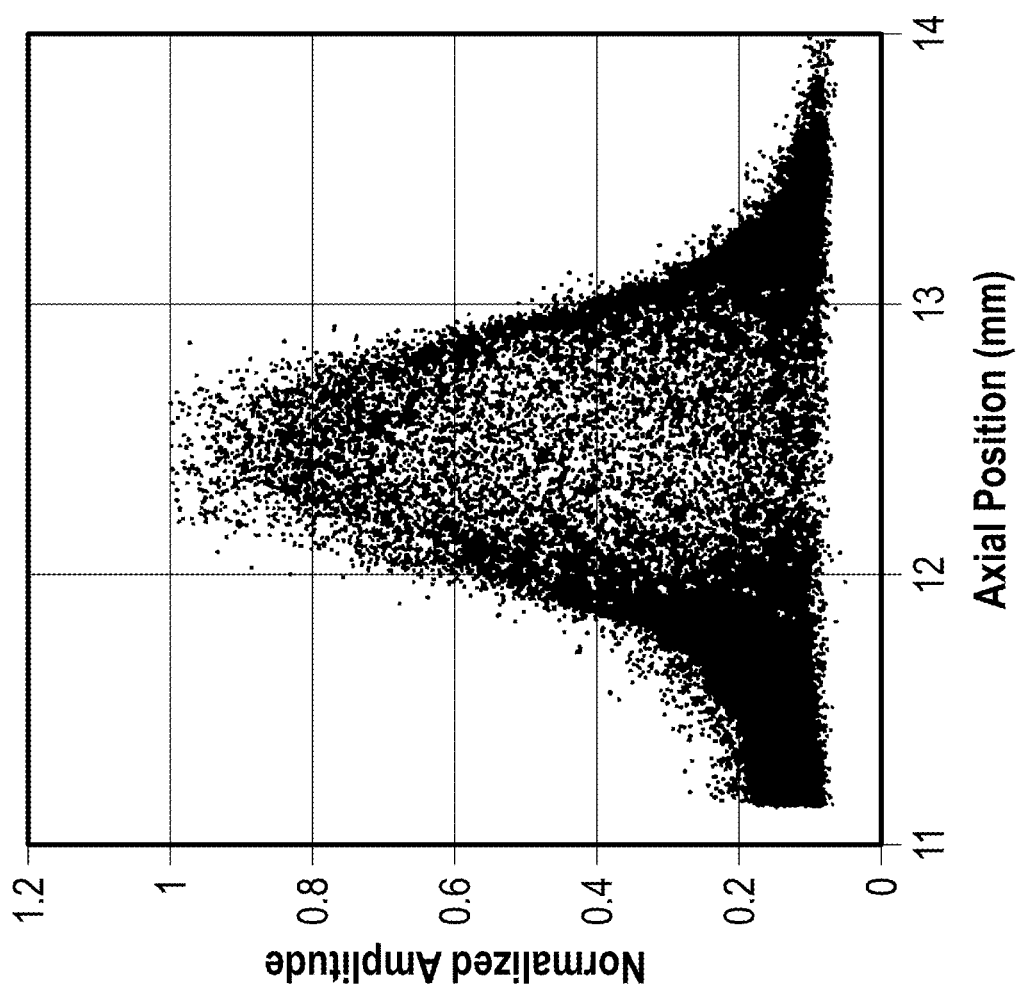
FIG. 10B is a scatter plot of normalized amplitude as a function of axial position for each detected echo in all measured frames of the B-mode ultrasound image of the exemplary 15 μm polystyrene microsphere suspension having a concentration of 25 particles/μL.
Figure 10C:
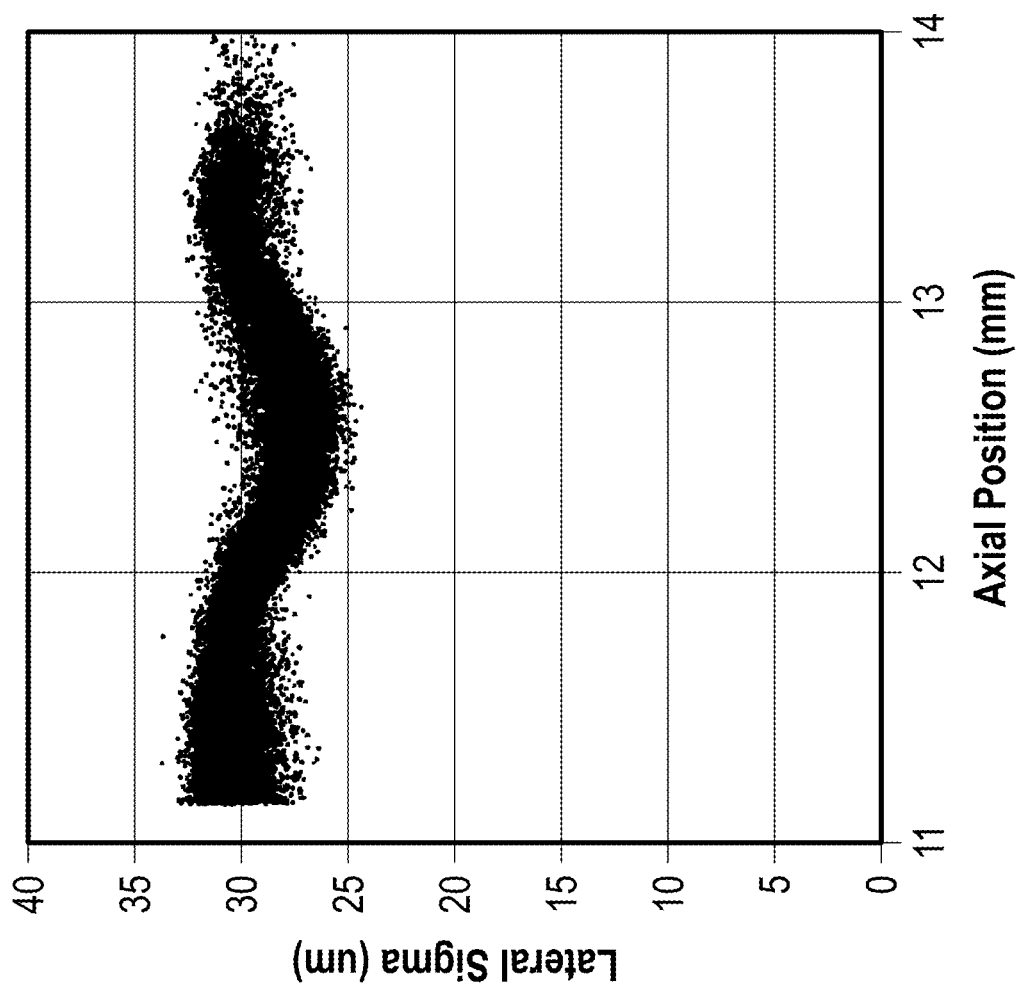
FIG. 10C is a scatter plot of lateral standard deviation as a function of axial position for each detected echo in all measured frames of the B-mode ultrasound image of the exemplary 15 μm polystyrene microsphere suspension having a concentration of 25 particles/μL.

The results of these determinations from an acquired 62 ultrasound image of the exemplary sample of 15 μm polystyrene microspheres with a concentration of 25 particles/μL are shown in FIGS. 10A-10C. In particular, FIG. 10A shows that the echo amplitude has no visible dependency on lateral position of the echo. Therefore, ignoring the effect near the edge of the transducer in the case of array imaging, the characteristics of the beam are substantially unchanged from one scan line to another, while a wide range of echo amplitudes is observed at a given lateral position. This difference is due to the differences in the axial and elevational positions of the scatterers.

As shown in FIG. 10B, the echo amplitude is strongly dependent on axial position, reaching a maximum around the focal point of the transducer, which is 12.7 for the MS used to acquire 62 the B-mode ultrasound image. Further, a large range of echo amplitude exists at a given axial position. Given that the echo amplitude does not depend on the lateral position (FIG. 10A), this variation of echo amplitude at a given axial position should be understood to result from differences in the elevational position of the scatterers producing the detected echoes. Thus, the elevational position of a given scatterer has a strong effect on the respective echo amplitude. In particular, echo amplitude reaches a maximum when the observed scatterer is located on the imaging plane, and decreases as the elevational location of the scatter deviates away from the imaging plane.

As shown in FIG. 10C, the lateral standard deviation of the echo envelope for the detected echoes shows some dependence on the axial position of the echo. At a given axial position, however, there is little variation. Accordingly, while the echo amplitude is strongly affected by the elevational position of the respective echo, the lateral standard deviation of the respective echo envelope and, therefore, the SSF remains relatively constant such that the SSF can be considered constant for all echoes at a given axial position. As described in greater detail below, determining 66 the effective volume of the acquired 62 ultrasound image can be accurately based on this assumption of a substantially constant SSF.

Figure 11:
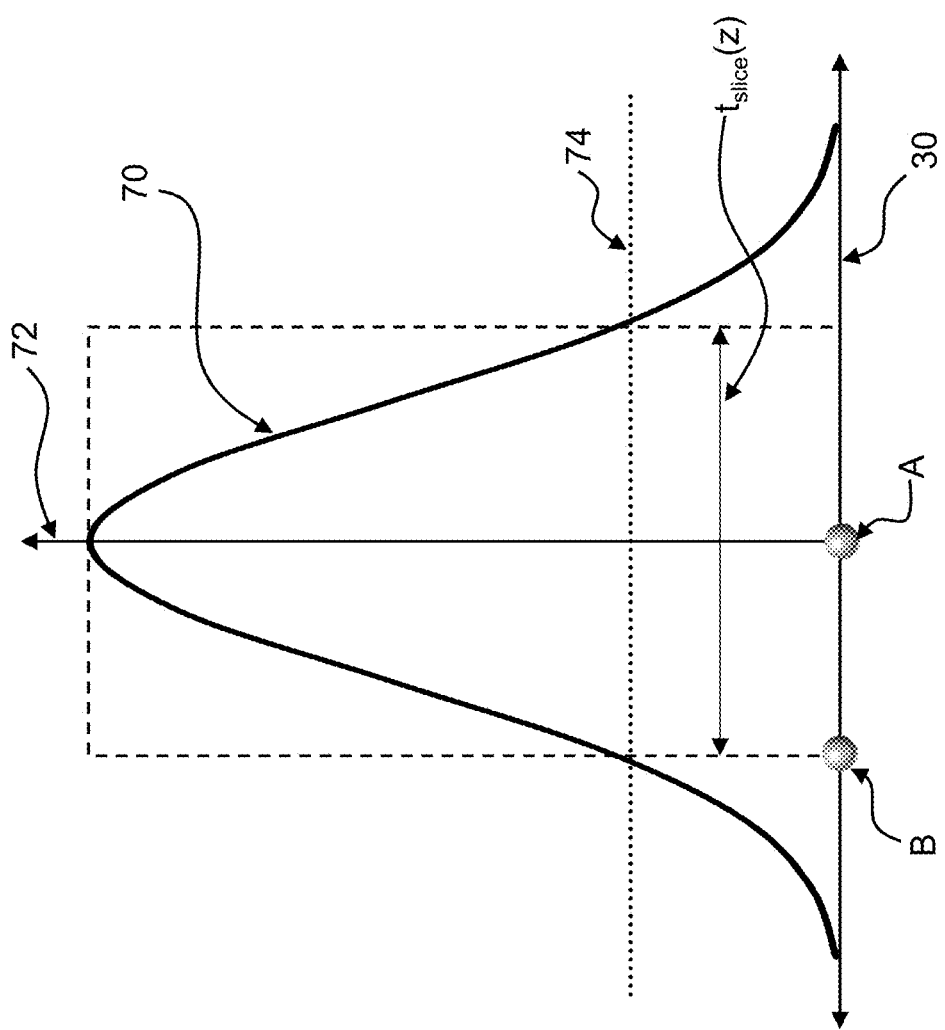
FIG. 11 is a schematic representation of an elevational beam profile superimposed on scatterers suspended in a medium, the scatterers are at equal axial positions and separated along an elevational axis.

Referring now to FIG. 11, the relationship between echo amplitude 70 and elevational position of a scatterer along elevational axis 30 is shown schematically for two scatterers, A and B, at the same axial position. Because the scatterers A and B are at the same axial position and because the effect of lateral position on echo amplitude is negligible, the detected difference in echo amplitude of A and B is the result of the difference in the elevational position of the scatterers, along the elevational axis 30, relative to an imaging plane 72. In particular, acoustic energy is highest on the imaging plane 72 and decreases away from the imaging plane 72. Therefore, scatterer A, which is exactly on the imaging plane 72, will produce the highest amplitude echo. Scatterer B, which is away from the imaging plane 72 will produce a lower echo amplitude relative to the echo amplitude of scatterer A. Further, at sufficiently large distances from the imaging plane 72, the echo amplitude of scatterer B is below a detection threshold 74. Accordingly, the highest echo amplitude represents a scatterer (scatterer A) on the imaging plane 72, and the lowest echo amplitude represents a scatterer (scatterer B) at the detection threshold 74. An effective slice thickness $t_{slice}(z)$, then, can be determined from the echo amplitude of scatterer A and scatterer B at an axial position z.

In implementations in which imaging is performed using a radially-symmetric transducer, which has a circular cross-sectional beam shape (e.g., such as the MS described herein), the effective elevational beam profile is identical to the effective lateral beam profile. The effective lateral beam profile is a substantially Gaussian function with a standard deviation $\sigma_{SSFx}$. Accordingly, the effective elevational beam profile is also a substantially Gaussian function with a standard deviation of $\sigma_{SSFx}$. The elevational position of scatterer A and scatterer B can be determined based on this relationship. Thus, for example, where scatterer A is the highest echo amplitude (on the imaging plane 72) and scatterer B is the lowest echo amplitude (at the detection threshold 74), the effective slice thickness can be determined based on the elevational beam profile being a substantially Gaussian function with a standard deviation $\sigma_{SSFx}$.

In these implementations in which imaging is performed using a radially-symmetric transducer, the effective elevational beam profile $P_y$ is represented as:

$$P_y = a_{scatA} \exp\left(-\frac{y^2}{2\sigma_{SSFx}^2}\right) \quad \text{(Eq. 2)}$$

where y is the distance along the elevational axis 30 and $a_{scatA}$ is the amplitude of the echo from scatterer A, which is the amplitude of the Gaussian function because $a_{scatA}$ is produced when scatterer A is at the imaging plane (y=0). Using Eq. 2, the beam profile for scatterer B can be expressed as:

$$a_{scatB} = a_{scatA} \exp\left(-\frac{y_{scatB}^2}{2\sigma_{SSFx}^2}\right) \quad \text{(Eq. 3)}$$

where $a_{scatB}$ is the amplitude of the echo from scatterer B and $y_{scatB}$ is the distance of scatterer B along the elevational axis 30. Solving for $y_{scatB}$ produces the following result:

$$y_{scatB} = \pm \sigma_{SSFx} \sqrt{2 \ln\left(\frac{a_{scatA}}{a_{scatB}}\right)} \quad \text{(Eq. 4)}$$

Thus, it should be appreciated that there are two possible positions of scatterer B, either in front of the imaging plane 72 or behind the imaging plane 72. Additionally, since scatterer B produced the lowest observed amplitude echo, scatterer B must have deviated the farthest away from the imaging plane among all of the observed echoes. Accordingly, the two possible locations represented in Eq. 4 also define the slice thickness $t_{slice}(z)$ of the image at the given axial position (z) as follows:

$$t_{slice}(z) = 2\sigma_{SSFx} \sqrt{2 \ln\left(\frac{a_{scatA}}{a_{scatB}}\right)} \quad \text{(Eq. 5)}$$

Referring now to FIGS. 6 and 11, determining 66 the effective volume of the acquired 62 ultrasound image can be based on the observed maximum and minimum echo amplitudes at a given axial position and the standard deviation of the spreading at the given axial position, which are parameters available from the acquired 62 ultrasound image. For example, in implementations in which imaging is performed using a radially-symmetric transducer, determining 66 the effective volume can include determining the effective slice thickness $t_{slice}(z)$ at a given axial position (z) according to Eq. 5. As described in greater detail below, the effective slice thickness can be used to determine an effective slice volume, and determination 66 of the effective volume can be based on a plurality of effective slice volumes (e.g., a sum of a plurality of effective slice volumes).

While the effective slice thickness $t_{slice}(z)$ has been described for implementations in which imaging is performed using a radially-symmetric transducer, other implementations are additionally or alternatively possible. For example, in certain implementations, the transducer can be asymmetrical (e.g., elliptical) such as in a linear array. An example of an ultrasound imaging using such a linear array is a VisualSonics Vevo 2100, model MS550D (Vevo), available from VisualSonics, Toronto, Canada. The Vevo has 40 MHz center frequency with −6 dB bandwidth of 82.5% spanning 22-66 MHz and geometric focus at 7 mm. The width (lateral dimension) of the image is 8 mm, consisting of 220 scan lines spaced by 36 μm and the depth (axial dimension) is 10 mm.

For an asymmetric transducer, the pulse-echo beam profile in the lateral direction is different than the pulse-echo beam profile in the elevational direction. To accommodate this asymmetry, Eq. 5 can be generalized as follows:

$$t_{slice}(z) = 2R_e \sigma_{SSFx} \sqrt{2 \ln\left(\frac{a_{scatA}}{a_{scatB}}\right)} \quad \text{(Eq. 6)}$$

where $R_e$ is the ratio of the scatterer spreading in the elevational direction to the scatterer spreading in the lateral direction, expressed as:

$$R_e = \frac{\sigma_{SSFy}}{\sigma_{SSFx}} \quad \text{(Eq. 7)}$$

The lateral SSF ($\sigma_{SSFy}$) can be measured from the acquired 62 image and, in certain implementations, the elevational SSF ($\sigma_{SSFx}$) can be measured by scanning the elevational direction. Alternatively, $R_e$ can be based on the measurement of the ratio between the elevational beam profile and the lateral beam profile. This is because the elevational beam profile is affected by a scatterer in the same way that the lateral beam profile is affected by the scatterer. Therefore, while both the lateral SSF ($\sigma_{SSFy}$) and the elevational SSF ($\sigma_{SSFx}$) depend on the type of sample being imaged, the ratio of the two is independent of the scatterer. Accordingly, $R_e$ can be based on a characterization of the imaging system alone (e.g., independent of the sample) and is, therefore, expressed as:

$$R_e = \frac{\sigma_{SSFy}}{\sigma_{SSFx}} \cong \frac{\sigma_y}{\sigma_x} \quad \text{(Eq. 8)}$$

where $\sigma_x$ is the standard deviation characterizing the lateral beam profile and $\sigma_y$ is the standard deviation characterizing the elevational beam profile. In some implementations, the ratio between the elevational beam profile and the lateral beam profile is simulated using an ultrasound simulation program.

Figure 12:
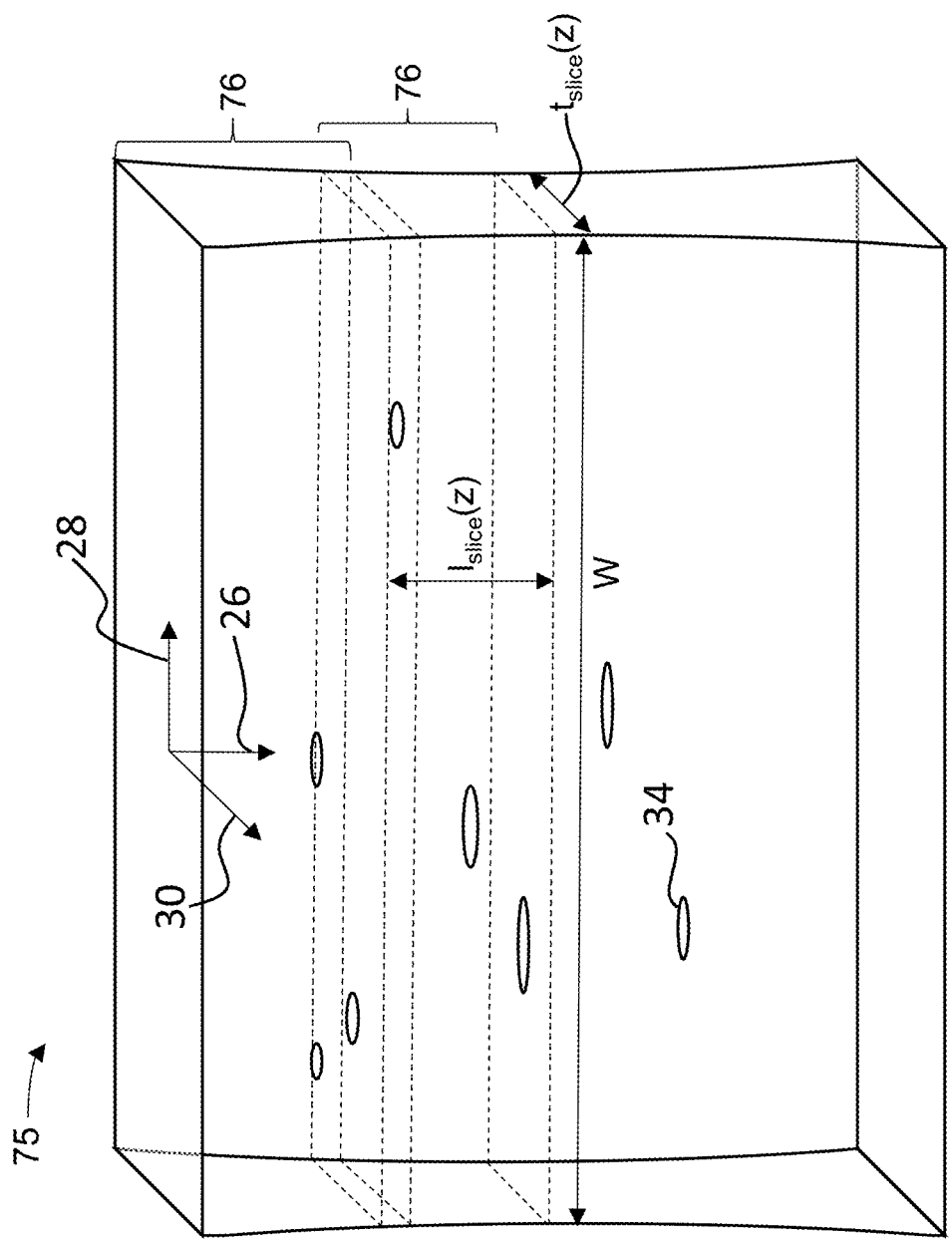
FIG. 12 is a schematic representation of axial slicing of an ultrasound image.

Referring now to FIGS. 6 and 12, determining 66 the effective volume can include dividing the acquired 62 ultrasound image 75 into axial slices 76. Such axial slicing can, for example, account for the strong dependence of echo characteristics on axial position. The axial slices 76 can, for example, overlap one another, providing some degree of redundancy in determining 66 the effective volume. The length of the axial slices 76 and the amount of overlap between the adjacent slices can be chosen, for example, based on characteristics of the transducer, such as the frequency and the f-number. For each axial slice 76, the maximum observed echo amplitude (A), the minimum observed echo amplitude (B), and the average lateral standard deviation ($\sigma_{SSFx}$) can be determined such that $t_{slice}(z)$ can be determined according to Eq. 6.

Figure 13:
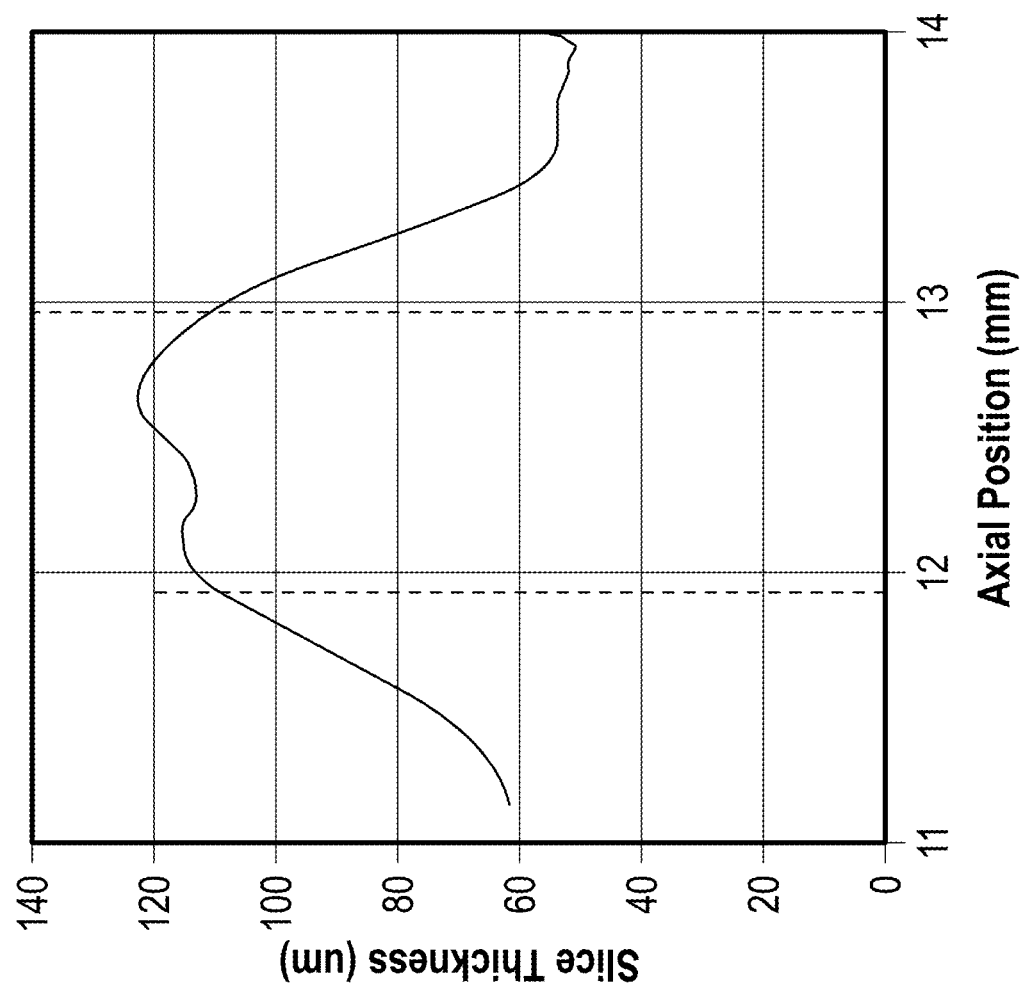
FIG. 13 is a graph of effective slice thickness as a function of axial position for the B-mode ultrasound image of the exemplary 15 μm polystyrene microsphere suspension having a concentration of 25 particles/μL.

Referring now to FIG. 13 and continuing with analysis of the B-mode ultrasound image of the exemplary 15 μm polystyrene microsphere suspension (25 particles/μL), effective slice thickness $t_{slice}(z)$ for axial slices are shown as a function of axial position. As shown, the effective slice thickness $t_{slice}(z)$ reaches a maximum around the focal point of the transducer and decreases moving away from it.

Referring again to FIGS. 6 and 12, given that the image width (W) and the axial slice 76 length ($l_{zslice}$) are defined, the effective slice volume $V_{slice}(z)$ can be determined as follows:

$$V_{slice}(z) = W \times l_{zslice} \times t_{slice}(z) \quad \text{(Eq. 9)}$$

$V_{slice}(z)$ can be determined for each axial slice 76 to determine 66 the effective volume of the ultrasound image. For example, determining 66 the effective volume of the ultrasound image can include summing $V_{slice}(z)$ determined for each axial slice 76. Based on $t_{slice}(z)$ and, thus, $V_{slice}(z)$, it should be appreciated that the determined 66 effective volume of the acquired 62 ultrasound image is not just a function of the imaging system, but also depends on the sample being imaged.

In terms of particle type, the more echogenic the particle, whether due to size, shape, or acoustic impedance, the larger the effective slice thickness $t_{slice}(z)$ and, thus, the larger the determined 66 effective volume. That is, a more echogenic particle can be further away from the image plane 72 and still produce a high enough echo to be detected in the resulting B-mode ultrasound image, resulting in a larger effective slice thickness $t_{slice}(z)$ and, thus, a larger determined 66 effective volume. By way of comparison, a less echogenic particle must be closer to the image plane 72 for its echo to be detected on the B-mode ultrasound image, which means that the effective slice thickness $t_{slice}(z)$ is smaller.

With respect to the medium in which the scatterers are suspended, a less attenuative medium results in a larger image volume, while a more attenuative medium results in a smaller volume. This is because attenuation of the medium results in decreased incident and reflected acoustic energy, which means that a particle must be closer to the image plane 72 for the particle to be detected in the resulting image. Similarly, any additional attenuative layers in the path of the acoustic wave will tend to reduce the effective image volume. This may be an important factor, for example, in clinical applications such as cerebrospinal fluid sampling where bodily fluids are imaged through skin and/or fat layers.

Figure 14:
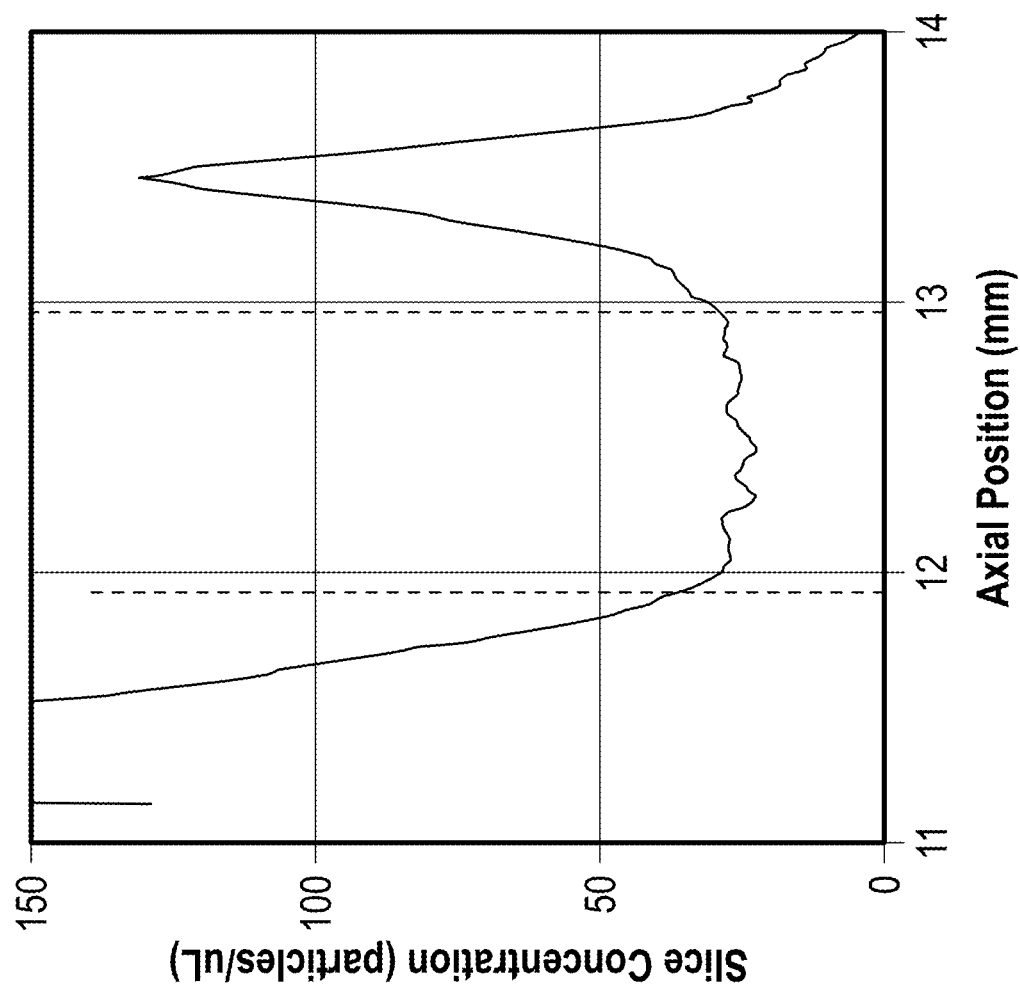
FIG. 14 is a graph of absolute slice concentration as a function of axial position for the B-mode ultrasound image of the exemplary 15 μm polystyrene microsphere suspension having a concentration of 25 particles/μL.

Referring now to FIGS. 6 and 14, determining 68 the absolute concentration of the effective volume is based on the counted 64 scatterers and the determined 66 effective volume. For example, counting 64 the scatterers can include counting scatterers in each of the axial slices 76 such that absolute slice concentration $C_{slice}(z)$ for each respective slice is expressed as:

$$C_{slice}(z) = \frac{N_{slice}(z)}{V_{slice}(z)} \quad \text{(Eq. 10)}$$

where $N_{slice}(z)$ is the counted number of echoes in the respective axial slice 76. Thus, determining 68 the absolute concentration can include averaging the absolute slice concentrations $C_{slice}(z)$ of at least some of the axial slices 76.

The slice concentration $C_{slice}(z)$ as a function of axial position of the B-mode ultrasound image of the exemplary 15 μm polystyrene microsphere suspension (25 particles/μL) is shown in FIG. 14. As shown, the absolute slice concentration can vary depending on the axial position, reaching a significantly higher concentration in the axial slices that are away from the focus. This variation can be due to noisy or faulty detection arising from low beam intensity in those slices away from the focus. Since the beam diverges, the echoes will tend to be weaker but wider, which can lead to over-counting of the echoes while the amplitude of the echoes and the effective slice thickness are accurately determined. This can lead to inaccuracies in the calculated concentration for low intensity slices.

In view of inaccuracies that can be associated with low intensity slices, determining 68 the absolute concentration can include applying a predetermined cutoff based on an amplitude range of echoes. For example, given that each slice has a respective maximum echo amplitude, determining 68 the absolute concentration can be based on the respective axial slices corresponding to a predetermined cutoff of maximum echo amplitudes. Thus, in certain implementations, determining 68 the absolute concentration can be based on the respective axial slices corresponding to the top 50 percent of maximum echo amplitudes.

The following experiments describe a determination of absolute particle concentration in accordance with the exemplary methods described herein. It is to be understood that these experiments and corresponding results are set forth by way of example only, and nothing in these examples shall be construed as a limitation on the overall scope of this disclosure.

Six experiments were performed using different types of samples consisting of both non-biological and biological particles. The details of the experiments are summarized in Table 1. In experiments 1-4, monodispersed samples of non-biological particles of different types were measured using the MS and Vevo, demonstrating the methods described herein with respect to different particle types and different imaging systems. In experiment 5, polydispersed samples including 10 μm and 15 μm polystyrene (PS) microspheres were measured, demonstrating classification of particles using BSC and measurement of concentration for each type of particle present in the sample. In experiment 6, T-cells suspended in phosphate buffered solution (PBS) were measured, demonstrating the methods described herein as applied to non-ideal biological samples.

TABLE 1

Summary of experiments performed.

| Experiment | Imaging System | Particle Type | Suspension Fluid |
|---|---|---|---|
| 1 | MS | 10 μm PS | Distilled $H_2O$ |
| 2 | Vevo | 10 μm PS | Distilled $H_2O$ |
| 3 | MS | 15 μm PS | Distilled $H_2O$ |
| 4 | MS | 10 μm $SiO_2$ | Distilled $H_2O$ |
| 5 | MS | 10 μm PS + 15 μm PS | Distilled $H_2O$ |
| 6 | Vevo | T-cells | PBS |

In experiments 1-6, reference concentration measurements were performed using disposable Fuchs-Rosenthal (FR) hemocytometers (DHC-F01, available from INCYTO of South Korea). Each sample was measured four times, consistent with the standards used in clinical laboratories for CSF cell counts. The concentration associated with the hemocytometer measurements was determined by averaging the four measurements.

A measurement error for the hemocytometer measurements was determined using a combination of two known methods. The first method estimates the standard deviation of the counts as the square root of the mean. The second method is based on the typical error achieved by trained technicians, which can be up to 15% in instances in which the concentration is relatively high and increases for low concentrations. Thus, for experiments 1-6, the first method was used for lower concentration samples, corresponding to 10 particles/μL. and the second method of 15% error was used for higher concentration samples.

A measurement error associated with the ultrasound imaging measurements was determined using the bootstrap method. Each measurement included 500 frames in the case of MS and 250 frames in the case of Vevo. Bootstrap is performed by resampling (with replacement) the frames 1,000 times. The error bars for the proposed method represent the 95% confidence interval.

Experiments 1 and 2

In experiments 1 and 2, ultrasound images of ten samples with different concentrations of 10 μm PS microspheres were acquired with MS and Vevo, respectively. The concentrations of the samples ranged from 0.5-200 particles/μL. The concentrations of the samples were determined from the respective ultrasound images of the samples using the methods described herein. Hemocytometer measurements were then acquired for the ten samples.

Figure 15:
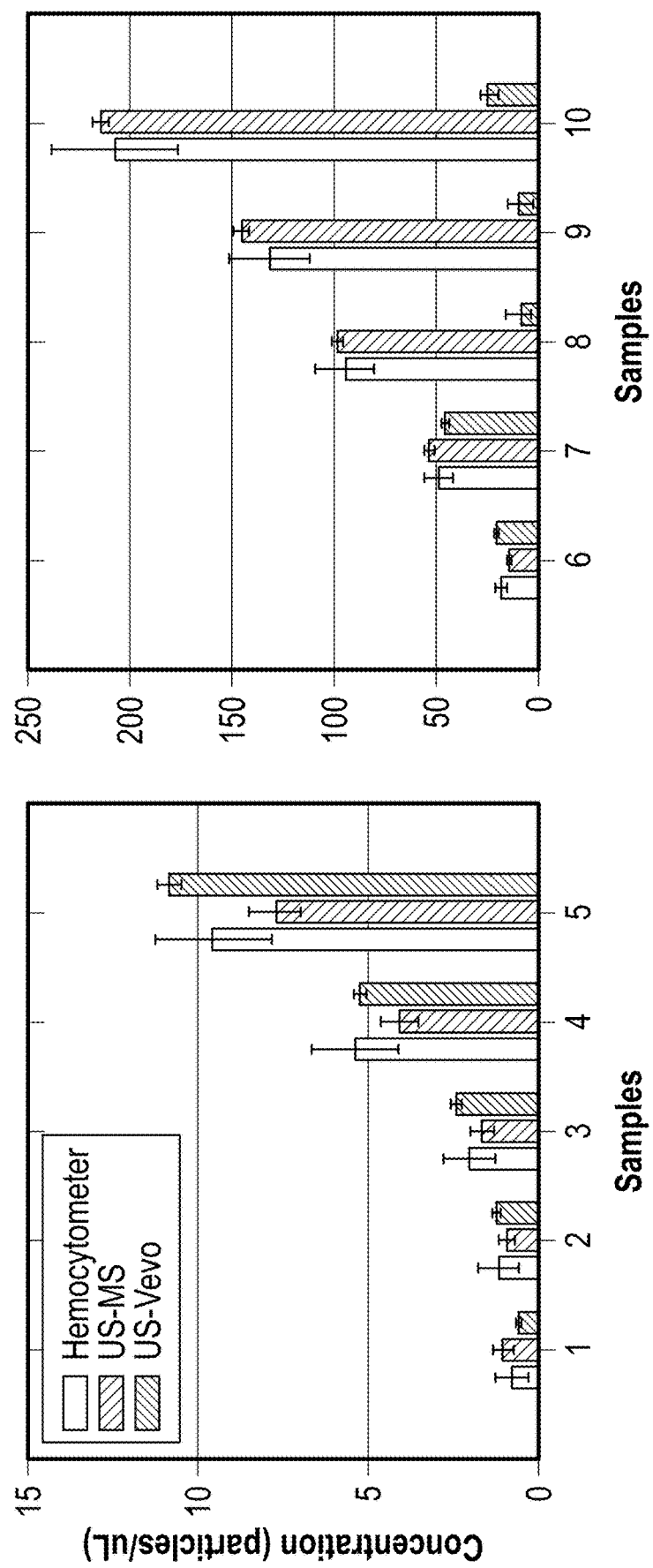
FIG. 15 is a graph of concentration measurement results from ultrasound images compared to concentration measurements from a hemocytometer for ten samples of 10 μm polystyrene microspheres suspended in distilled water and having concentrations ranging from 0.5-200 particles/μL.

Referring now to FIG. 15, the concentrations determined from the MS ultrasound images of the ten samples were in good agreement with the hemocytometer measurements up to 200 particles/μL, while the concentrations from the Vevo ultrasound images of the ten samples were in good agreement with the hemocytometer measurements up to 50 particles/μL. Without wishing to be bound by theory, the ultrasound-determined concentration is believed to deviate from the hemocytometer measurements at higher concentrations because the methods of the present disclosure require detection of individual particles in the ultrasound image and, when the concentration is high and there are too many echoes visible in the image, the methods of the present disclosure can undercount the particles. The maximum measurable concentration is different for the measurements made with the MS and Vevo. Again, without wishing to be bound by theory, this is believed to be because the effective slice thickness of the image is larger for the Vevo than MS due to various factors including differences in the acoustic output energy, signal-to-noise ratio of the system, and beam shape. Also, because the effective volume calculation relies on the scatterer spread function for echoes detected within the beam, there is an effective floor of a low concentration below which lower concentrations cannot be accurately measure. Thus, as with any instrumentation, it is believed that there are practical upper and lower limits to concentrations that can be accurately determined using the techniques described herein.

Experiments 3 and 4

In experiment 3, seven samples of 15 μm PS microspheres with concentration ranging from 0.5-60 particles/μL were measured using MS ultrasound. In experiment 4, nine samples of 10 μm silica ($SiO_3$) microspheres with concentration ranging from 0.5-120 particles/μL were measured using MS ultrasound. These experiments demonstrate, for example, that the methods described herein are applicable to different sizes and types of particles without the requirement of specific calibration for the different sizes and types of particles.

Figure 16A:
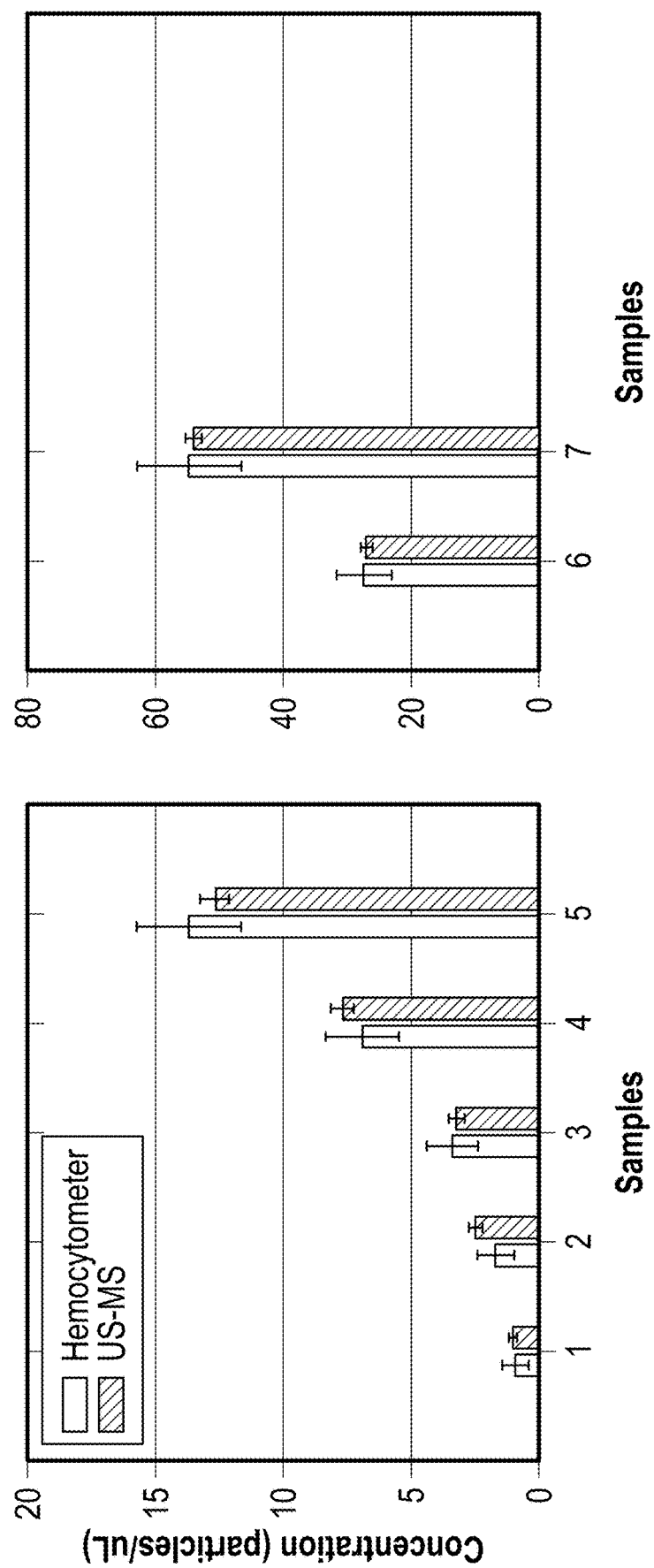
FIG. 16A is a graph of concentration measurement results from ultrasound images compared to concentration measurements from a hemocytometer for seven samples of 15 μm polystyrene microspheres suspended in distilled water and having concentrations ranging from 0.5-60 particles/μL.
Figure 16B:
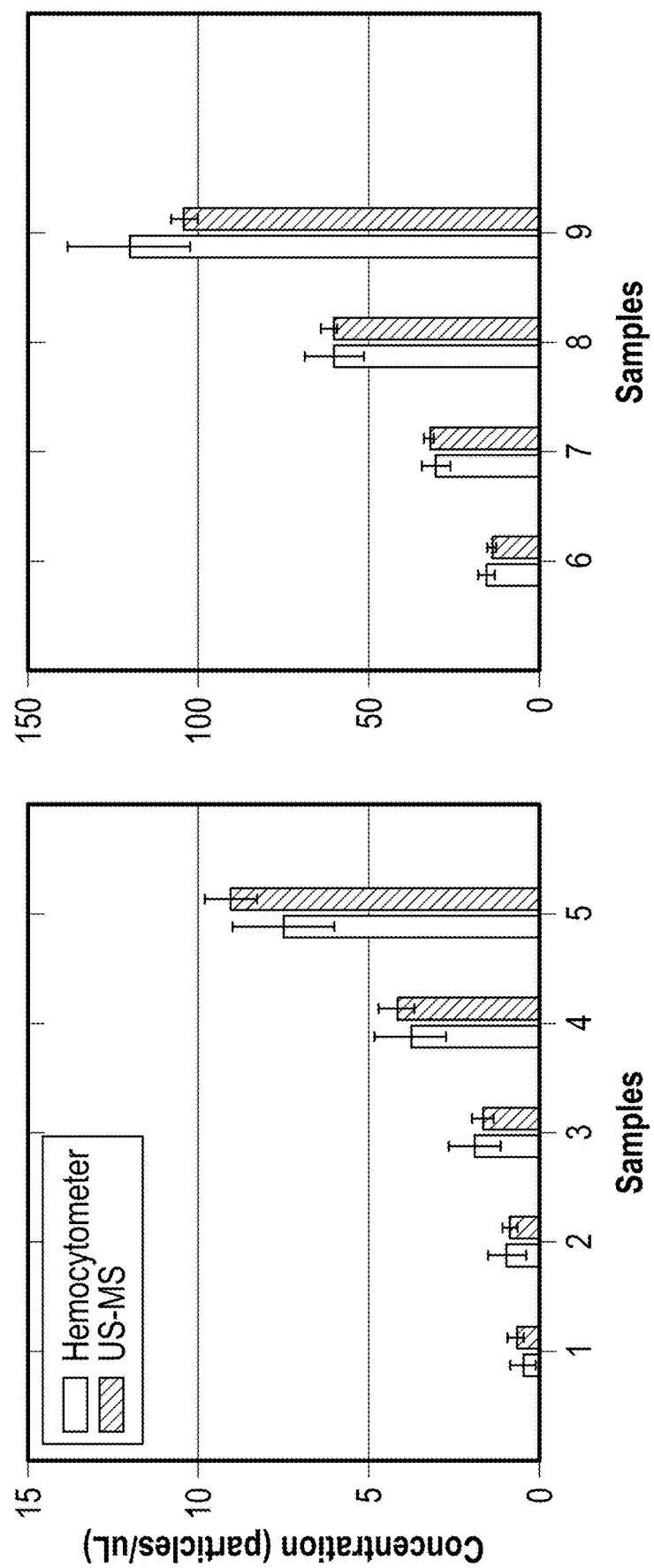
FIG. 16B is a graph of concentration measurement results from ultrasound images compared to concentration measurements from a hemocytometer for nine samples of 10 μm silica microspheres suspended in distilled water with concentration ranging from 0.5-120 particles/μL.

Referring now to FIG. 16A and FIG. 16B, the results of experiment 3 and experiment 4 are shown, respectively. As shown, both 15 μm PS and 10 μm silica microspheres demonstrated results similar to those of 10 μm PS microsphere samples. The concentrations determined according to the methods described herein were in good agreement with the hemocytometer measurement in the lower concentration range but deviate from the hemocytometer measurement in the higher concentration range. Using the methods described herein, the maximum measurable concentration appears to be about 60 particles/μL for the 15 μm PS microspheres measured with MS, and 120 particles/μL for the 10 μm silica microspheres measured with MS. As in experiments 1 and 2, the difference is due to the difference in the effective slice thickness, which, in the case of experiments 3 and 4, is believed to be caused by the difference in echogenicity of the particles, given that the imaging system is the same. The high echogenicity results in a larger number of echoes being visible in the image, for the same concentration, which leads to the differences in maximum measurable concentration observed in experiments 3 and 4.

Experiment 5

In experiment 5, polydispersed samples of 10 μm and 15 μm PS microspheres were measured with MS. Four samples were measured in which the 15 μm PS microsphere concentration was held constant while the concentrations of 10 μm PS microspheres were varied. This experiment demonstrates the performance of spectral analysis including BSC-based particle type classification to identify respective particle counts for the 10 μm and 15 μm PS microspheres. The respective particle counts determined according to these classifications were used to determine respective concentrations of each size of microsphere according to the presently disclosed methods. That is, the detected echoes corresponding to scatterers in the ultrasound image were classified into different particle types (e.g., 10 μm and 15 μm microspheres) and the steps of counting the scatterers, determining the effective volume, and determining an absolute concentration of the respective scatterers were performed for each classified particle type.

Referring now to FIG. 17, the concentrations determined according to the particle classification methods described herein were in good agreement with the hemocytometer measurements. Such agreement demonstrates that the particle classification described herein is effective for classifying particles of different sizes (e.g., classifying 10 μm particles and classifying 15 μm particles) and that determination of effective slice thickness, which is based on classification of the particle types, provides accurate results.

Figure 18:
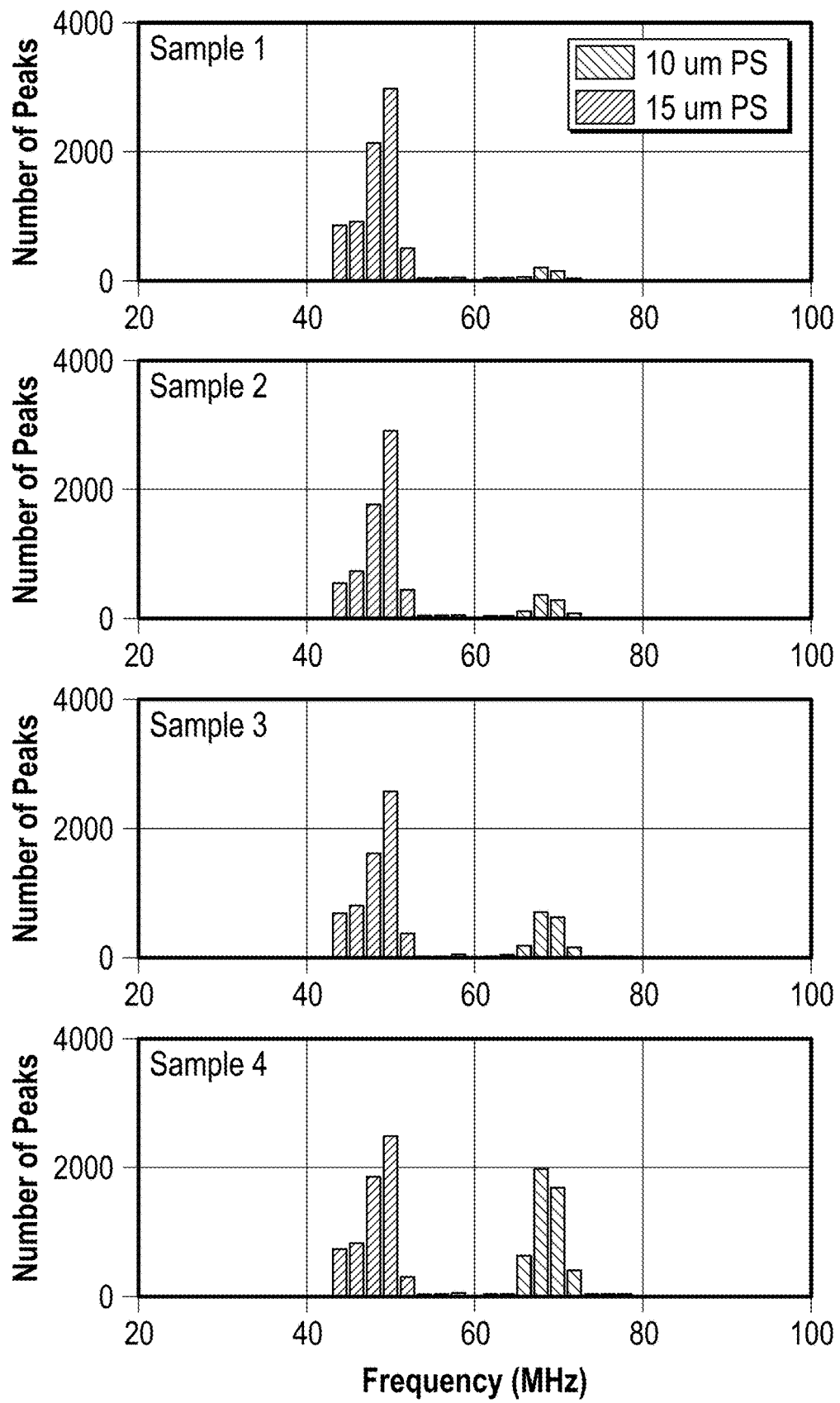
FIG. 18 is a histogram, for each sample in FIG. 17, of peak frequency in backscatter coefficient of detected echoes after classification.

Referring now to FIG. 18, a histogram of the peak frequency in the BSC of all detected particles after classification is shown. Although 15 μm PS microspheres have lower concentration, these cases show larger counts because the effective slice thickness is larger for 15 μm PS microspheres than for 10 μm microspheres. Thus the concentration for the 15 μm PS microspheres was calculated over a larger effective volume.

Experiment 6

In experiment 6, samples of T-cells suspended in PBS are imaged with the Vevo. This experiment demonstrated performance of the methods disclosed herein for non-ideal particles such as human cells. Experiments 1-5 were performed using ideal microspheres manufactured with controlled shape and size. Human cells, however, even those of the same type, can vary widely in terms of size and shape, depending on various factors such as environment, cell cycle, etc.

Figure 19:
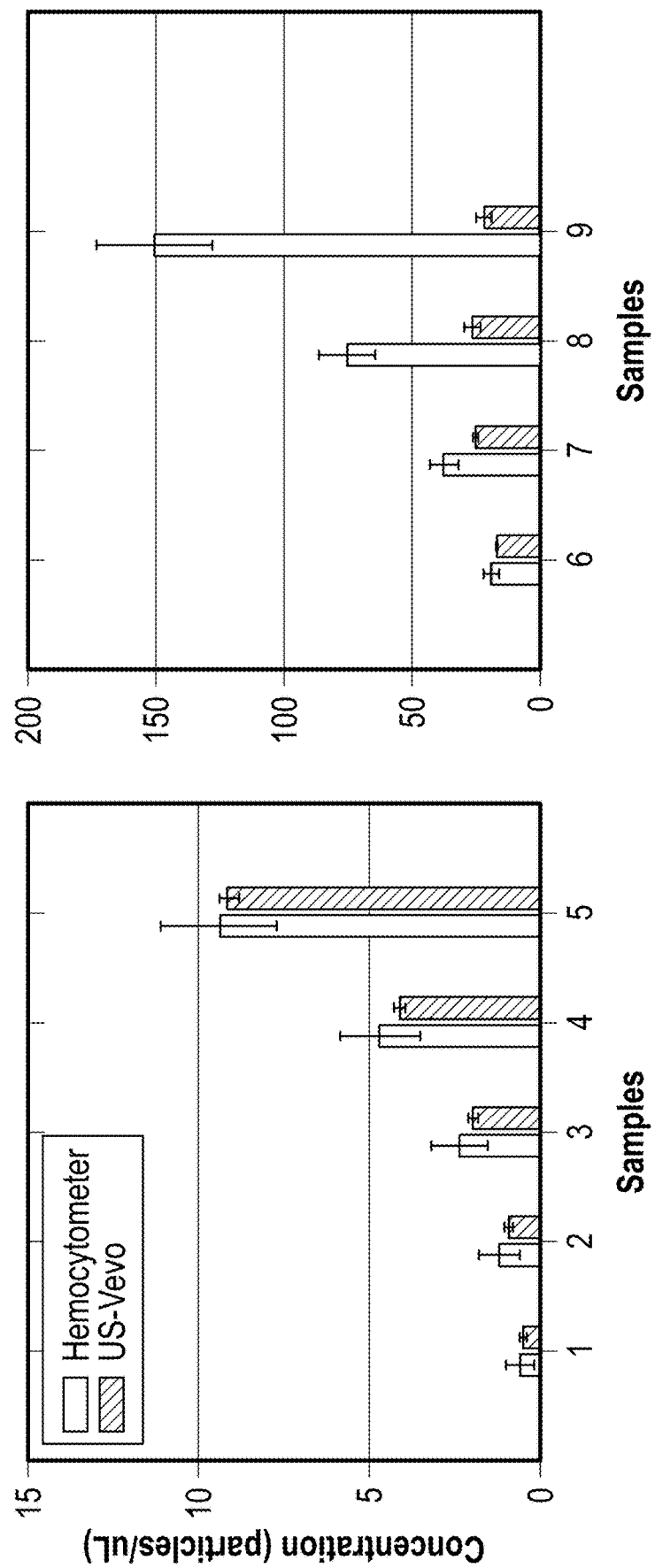
FIG. 19 is a graph of concentration measurement results from ultrasound images compared to concentration measurements from a hemocytometer for nine samples of T-cells suspended in phosphate-buffered solution.

Referring to FIG. 19, the concentration measurement determined from the ultrasound images according to the presently disclosed methods are in good agreement with the concentration measurements obtained with the hemocytometer. As shown, the agreement between the two types of measurements is good up to about 20 cells/μL. As with experiments 1-5, the concentration measurements according to the presently disclosed methods deviate from the hemocytometer measurements at higher concentrations.

In view of experiments 1-6, it should be appreciated that the dependence of effective slice thickness on the sample type and on the imaging system results in different maximum measurable concentration. In general, the larger the effective slice thickness, the lower the maximum measurable concentration using the methods described herein. The concentrations calculated using the ultrasound-based methods described herein deviate from the hemocytometer measurements due to failure in particle detection at relatively high concentrations. Accordingly, the maximum measurable concentration according to the methods described herein can be usefully increased by reducing the number of echoes that appear in the ultrasound image for a given concentration, such as by changing the focus or beam formation of the ultrasound transducer.

While certain implementations have been described, other implementations are additionally or alternatively possible. For example, where cells are difficult to detect or count in isolation, other particles may be added to a solution or sample that selectively bond to or otherwise associate with the cells in order to form a new particle with different, and more particularly, better, echo characteristics for detection. Thus the echogenicity of cells or other particles of interest may be improved by adding other particles that associate with the cells in order to change their size, shape, composition, or other properties so that they are more readily detected within an ultrasound image.

Figure 20:
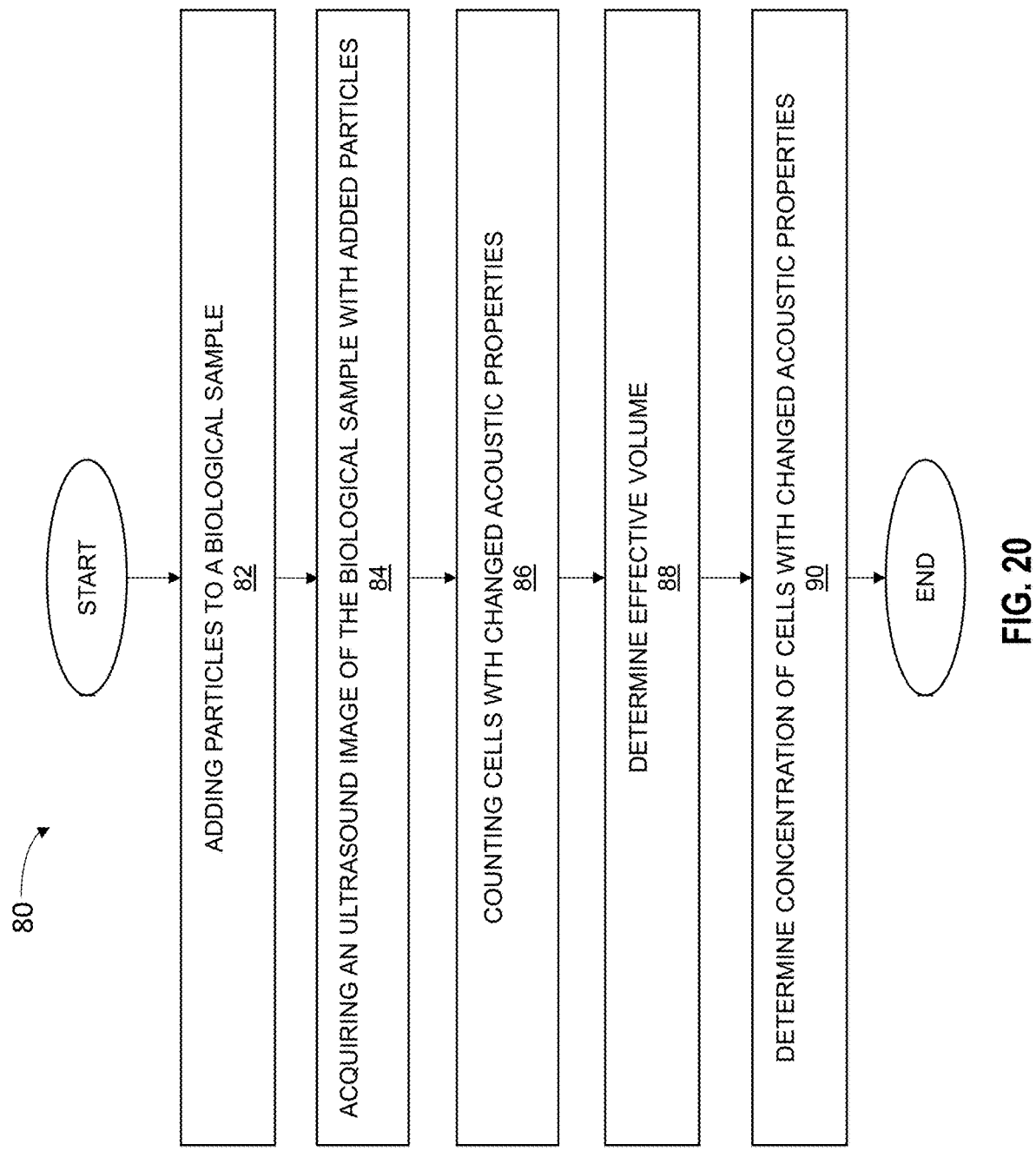
FIG. 20 is a flowchart of an exemplary method of determining absolute concentration of cells in a biological sample.

Referring to FIG. 20, this technique may be exploited to calculate the concentration of cells in a biological sample. There is disclosed in FIG. 20 an exemplary method 80 of determining absolute concentration of cells in a biological sample that includes adding 82 particles to a biological sample of cells in a medium, acquiring 84 a two-dimensional ultrasound image of the biological sample with the added particles, counting 86 cells in the ultrasound image with changed acoustic properties in the presence of the added particles, determining 88 an volume of at least a portion of the ultrasound image, and determining 90 an absolute concentration of the cells with changed acoustic properties in the biological sample. In general, as described in greater detail below, the cells have an affinity for the added 82 particles, and the added 82 particles change the acoustic properties of the cells such that, for example, the cells are more readily detectable (e.g., as a result of a change in size and/or a change in echogenicity).

Adding 82 particles can include, for example, adding polystyrene microspheres of known and detectable size (e.g., 10 μm polystyrene microspheres) to the biological sample. This addition 82 of particles can be, for example, in vitro. In general, adding 82 particles changes the acoustic properties of the cells such that the number of cells and the effective volume can be determined more accurately according to any of the methods described herein. For example, the cells attached to the added 82 particles can have a different (e.g., increased) size and/or different (e.g., increased) echogenicity relative to the cells without the added particles, such that the cells can be detected more easily and accurately within an ultrasound image.

In certain implementations, cells in the biological sample attach to the polystyrene microspheres. For example, in instances in which the biological sample includes T-cells, the T-cells will attach to the added 82 polystyrene particles as part of a normal immune response. Additionally, or alternatively, adding 82 particles can include the addition of particles coated with a reagent for which the cells of interest have an affinity.

Acquiring 84 a two-dimensional ultrasound image can include any of the methods of acquiring a two-dimensional ultrasound image described herein. Thus, for example, acquiring 84 a two-dimensional ultrasound image can include acquiring the image using a manually scanned and symmetric, single element, transducer such as the MS. Additionally, or alternatively, acquiring 84 a two-dimensional ultrasound image can include acquiring the image using a high frequency ultrasound imaging system including linear arrays, such as the Vevo.

Counting 86, in the ultrasound image, cells with changed acoustic properties in the presence of the added particles can be carried out according to any of the counting methods described herein. For example, counting 86 can include spectral analysis including BSC-based peak frequency detection. It should be appreciated that the addition of particles can change the acoustic properties of the cells such that the cells are more readily counted 86. For example, in instances in which the cells produce echoes that are below the detectable threshold in the acquired 84 ultrasound image, the addition of particles that are above the detectable threshold and become attached to the cells can facilitate subsequent counting 86 of the cells.

Determining 88 the effective volume of at least a portion of the ultrasound image can include determining effective volume according to any of the methods described herein. For example, the determining 88 the effective volume can include determining the elevational thickness of the two-dimensional ultrasound image based on the maximum and minimum detected echo amplitudes along a portion of the two-dimensional image. Thus, to the extent the added 82 particles change the echogenicity of the particles, the added 82 particles can increase the effective volume of the ultrasound image, thus increasing the determined 88 effective volume of the ultrasound image.

Determining 90 the absolute concentration of cells with changed acoustic properties can be based on the counted 86 cells with changed acoustic properties and the determined 88 effective volume. In general, determining 90 the absolute concentration of cells with changed acoustic properties can be carried out according to any of the methods of determining absolute concentration disclosed herein. Because determining 90 of the absolute concentration of cells according to the methods described herein can be less accurate in low-intensity portions (e.g., slices) of the ultrasound image, the addition of particles to increase intensity can improve the accuracy of the determined 90 absolute concentration relative to determinations of absolute concentration made without the addition of particles.

Figure 21:
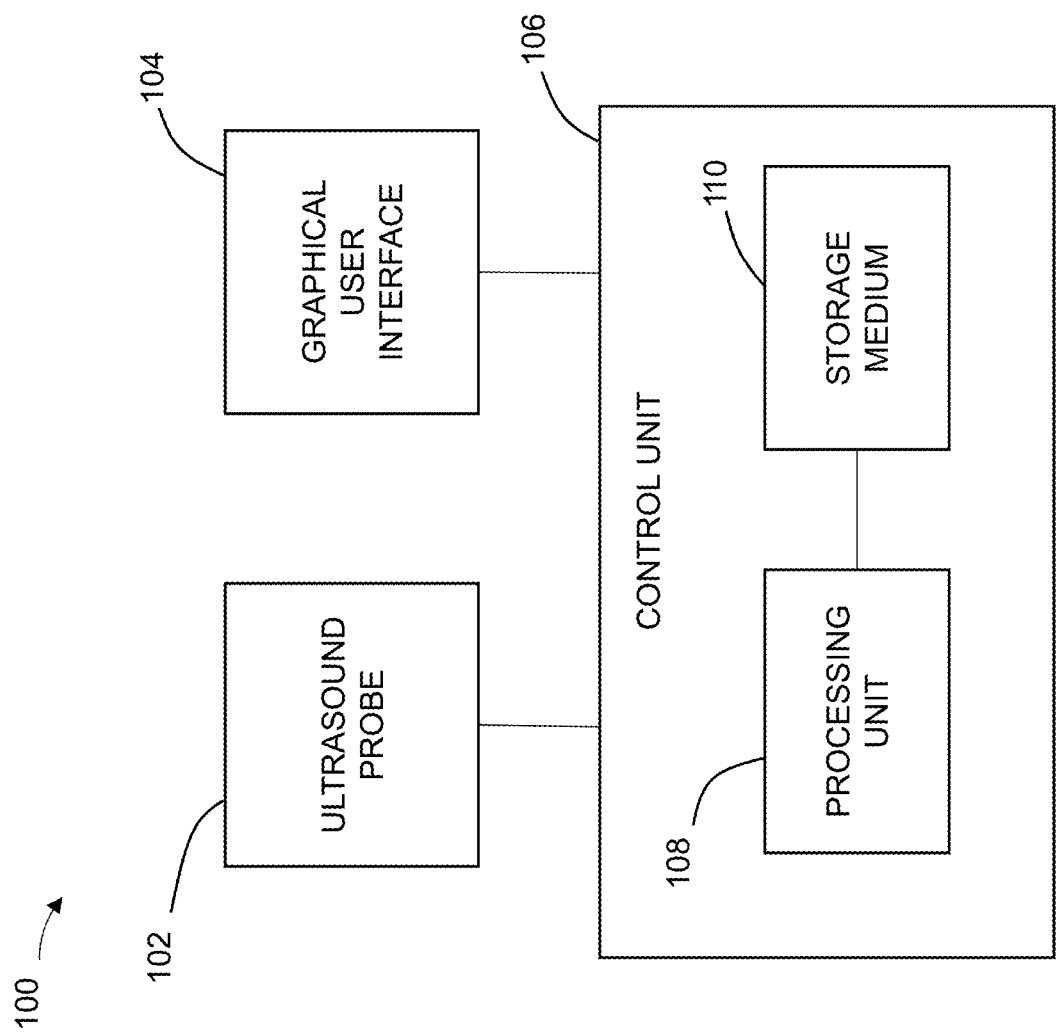
FIG. 21 is a schematic representation of an ultrasound system.
Figure 22:
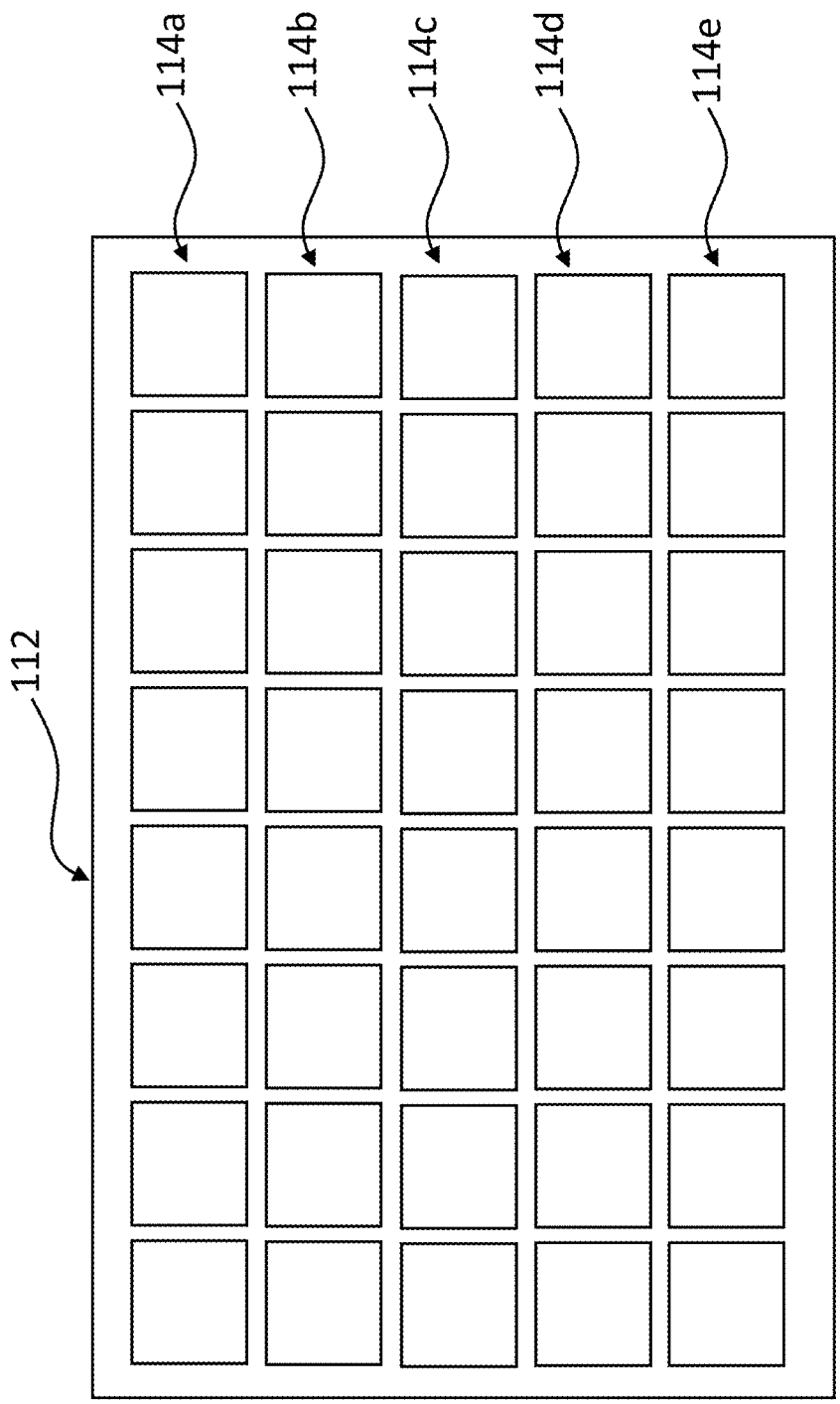
FIG. 22 is a schematic representation of an exemplary ultrasound transducer of the ultrasound system of FIG. 21.
Figure 23:
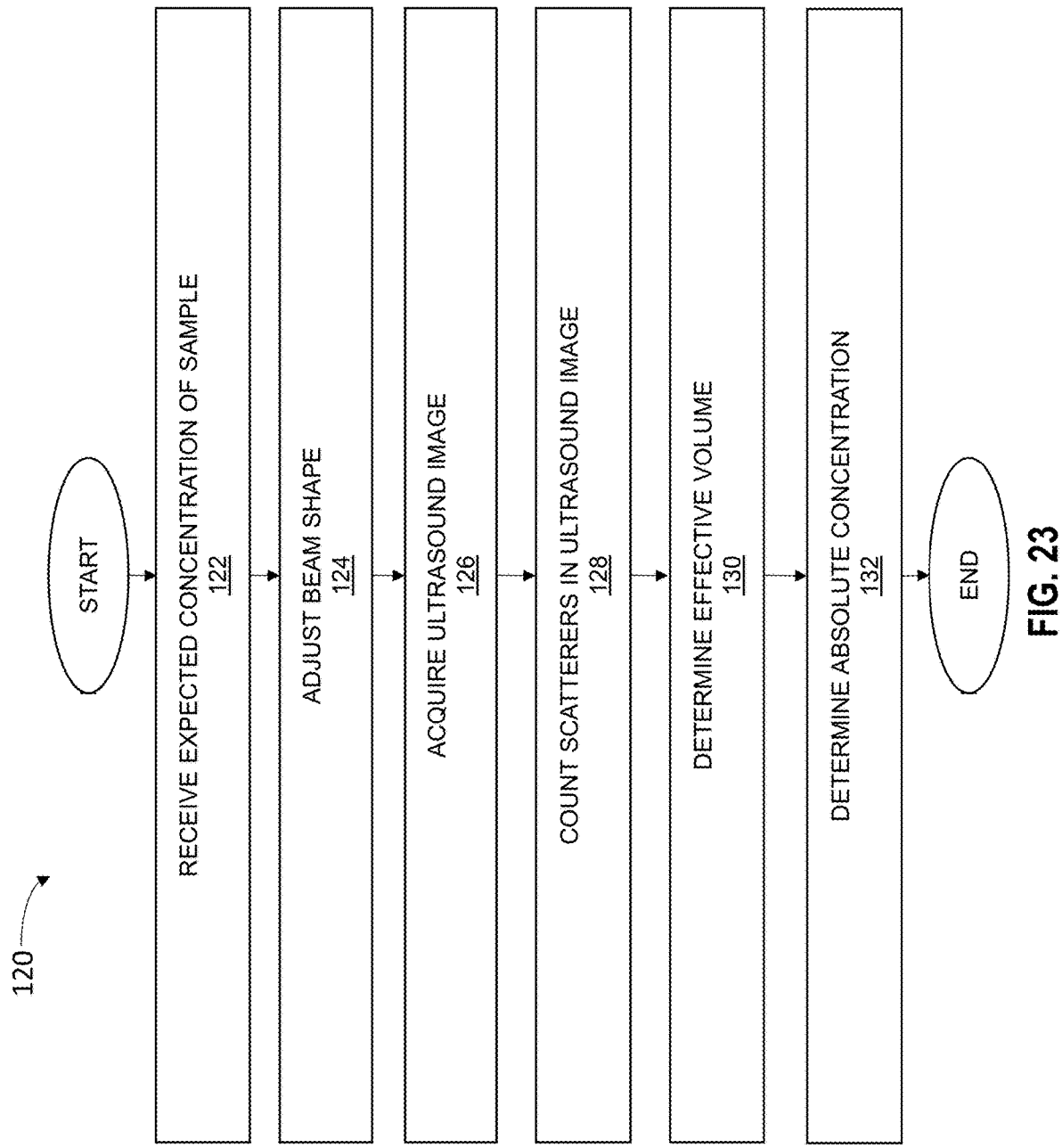
FIG. 23 is a flowchart of exemplary method of adjusting a beam width of an ultrasound transducer of the ultrasound system of FIG. 21.

As another example, while the measurement of absolute concentration of particles has been described as including ultrasound transducers of fixed geometry, other implementations are additionally or alternatively possible. For example, referring to FIGS. 21-23, a system 100 may include an ultrasound probe 102, a graphical user interface 104, and a control unit 106 in communication with the ultrasound probe 102. The controller 106 may include a processing unit 108 (e.g., one or more processors) and a non-transitory, computer-readable storage medium 110 having computer executable instructions for causing the one or more processors 108 to adjust the beam width of an ultrasound transducer 112 of the ultrasound probe 102 and carry out any of the exemplary methods described herein.

The ultrasound transducer 112 may have an adjustable beam shape that can be adjusted, for example, based on an expected concentration of a sample. For example, the ultrasound transducer 112 can have a beam shape that is adjustable in the elevational direction such that the volume of an acquired ultrasound image can be increased or decreased as desired. Increasing the beam width in the elevational direction can, for example, increase the number of echoes detected and, therefore, improve accuracy of the determination of an absolute concentration of scatterers in a medium under suitable conditions.

In some implementations, the ultrasound transducer 112 can include a plurality of rows 114*a-e* of piezoelectric elements in the elevational direction. In such implementations, the beam width of the ultrasound transducer 112 can be adjusted in the elevational direction by activating or deactivating one or more rows 114*a-e* of piezoelectric elements. For example, the beam width of the ultrasound transducer 112 can be increased in the elevational direction with respect to a beam width produced by the row 114*a* of piezoelectric elements by additionally activating row 114*b* of piezoelectric elements. Similarly, the beam width of the ultrasound transducer 112 can be increased in the elevational direction with respect to the beam width produced by rows 114*a* and 114*b* of piezoelectric elements by additionally activating row 114*c* of piezoelectric elements, and so forth. This flexibility may be used to adapt the effective volume for improved accuracy according to an expected or measured concentration of particles within the aggregated image.

The storage medium 110 of the control unit 106 can have computer executable instructions for causing the one or more processors 108 to execute the exemplary method 120 including receiving 122 an expected concentration of a sample, adjusting 124 the beam shape based on the received expected concentration, acquiring 126 a two-dimensional ultrasound image from the transducer, with the modified beam shape, of a medium containing a number of scatterers, counting 128 the scatterers in the ultrasound image, determining 130 an effective volume of a least a portion of the ultrasound image, and 132 determining an absolute concentration of the scatters in the medium.

Receiving 122 an expected concentration of a sample can include, for example, receiving an input from an input device (e.g., a keyboard and/or mouse) in communication with the control unit 106, or analyzing a preliminary image from the ultrasound transducer. Adjusting 124 the beam shape can include adjusting the elevational width of the beam shape, for example to increase the accuracy of the determined 132 absolute concentration. It should be appreciated that the steps of acquiring 126 the two-dimensional ultrasound image, counting 128 the scatterers in the ultrasound image, determining 130 the effective volume, and determining 132 the absolute concentration can be carried out according to any one or more of the exemplary methods described herein.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the devices, methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A method comprising:
   acquiring an ultrasound image of a medium with an ultrasound transducer, wherein the ultrasound image includes at least a portion of a two-dimensional image obtained from the ultrasound transducer and wherein the medium contains a number of scatterers;
   determining a volume of the ultrasound image in which one or more of the number of scatterers in the medium produce an echo detectable within the two-dimensional image;
   counting the scatterers in the ultrasound image; and
   based on the counted scatterers and the volume of the ultrasound image, determining an absolute concentration of the scatterers in the medium.

2. The method of claim 1, wherein determining the absolute concentration of the scatterers in the medium includes determining the absolute concentration of the scatterers without contacting the medium with a body of the ultrasound transducer.

3. The method of claim 1, wherein determining the volume of the ultrasound image is based on echogenicity of the scatterers and attenuation of the medium.

4. The method of claim 1, wherein determining the volume of the ultrasound image is based on a ratio of an elevational beam profile to a lateral beam profile.

5. The method of claim 1, wherein determining the volume of the two-dimensional image includes determining a beam thickness along an elevational axis of the ultrasound image, the elevational axis perpendicular to the two-dimensional image.

6. The method of claim 5, wherein determining the beam thickness includes slicing the ultrasound image into a plurality of slices along an axial axis of the ultrasound image, determining a slice thickness for each slice, and, based on the slice thickness, determining a slice volume.

7. The method of claim 6, wherein determining the slice thickness is based on an extent to which the counted scatterers, detected as echoes in the respective slice, deviate from an axis of the ultrasound transducer.

8. The method of claim 6, wherein determining the absolute concentration of the scatterers in the medium includes determining the absolute concentration of the scatterers in each slice.

9. The method of claim 8, wherein the absolute concentration of the scatterers in each slice is a ratio of the counted scatterers in the slice to the volume of the slice, the volume of the slice based on a lateral width of the image, axial length of the slice, and the thickness of the slice.

10. The method of claim 8, further comprising averaging at least some of the absolute slice concentrations.

11. The method of claim 10, wherein averaging at least some of the absolute slice concentrations includes averaging the absolute slice concentrations corresponding to a predetermined cutoff based on an amplitude range of echoes.

12. The method of claim 1, further comprising selecting scatterers of interest from the ultrasound image.

13. The method of claim 12, wherein selecting the scatterers of interest includes performing a spectral analysis of echoes in the ultrasound image.

14. The method of claim 13, wherein the spectral analysis of echoes in the ultrasound image is based on observed peak frequency in backscatter coefficient of the echoes in the ultrasound image.

15. The method of claim 12, wherein selecting the scatterers of interest includes classifying scatterers in the ultrasound image into different particle types, wherein the steps of counting the scatterers, determining the volume, and determining an absolute concentration of scatterers are performed for each classified particle type.

16. The method of claim 1, wherein acquiring the ultrasound image includes acquiring the ultrasound image from a radially symmetric ultrasound transducer.

17. The method of claim 1, wherein acquiring the ultrasound image includes acquiring the ultrasound image from a linear array transducer.

18. The method of claim 1, wherein the ultrasound image is a B-mode ultrasound image.

19. A method comprising:
adding particles to a biological sample of cells in a medium, the cells having an affinity for the added particles;
acquiring a two-dimensional ultrasound image, obtained by an ultrasound transducer, of the biological sample with the added particles;
counting, in the ultrasound image, cells with changed acoustic properties in a presence of the added particles;
determining a volume of at least a portion of the ultrasound image; and
based on the counted cells with changed acoustic properties and the volume of the ultrasound image, determining an absolute concentration of the cells with changed acoustic properties in the biological sample.

20. A system comprising:
an ultrasound transducer having an adjustable beam shape; and
a controller including one or more processors and a non-transitory, computer-readable storage medium having computer executable instructions for causing the one or more processors to:
receive an expected concentration of a sample,
adjust the beam shape based on the received expected concentration,
acquire a two-dimensional ultrasound image from the transducer, with the adjusted beam shape, of a medium containing a number of scatterers,
count the scatterers in the ultrasound image,
determine a volume of at least a portion of the ultrasound image, and
based on the counted scatterers and the volume of the ultrasound image, determine an absolute concentration of the scatterers in the medium.

* * * * *